(12) United States Patent
Goldberg

(10) Patent No.: US 6,274,703 B1
(45) Date of Patent: Aug. 14, 2001

(54) METHOD OF CELL SURFACE ACTIVATION AND INHIBITION

(75) Inventor: Gregory I. Goldberg, St. Louis, MO (US)

(73) Assignee: Washington University, St. Louis, MO (US)

( * ) Notice: Subject to any disclaimer, the term of this patent is extended or adjusted under 35 U.S.C. 154(b) by 0 days.

(21) Appl. No.: 09/138,721

(22) Filed: Aug. 24, 1998

Related U.S. Application Data

(62) Division of application No. 08/924,330, filed on Sep. 5, 1997, now Pat. No. 6,022,948.
(60) Provisional application No. 60/026,226, filed on Sep. 17, 1996.

(51) Int. Cl.[7] .................................................. C07K 14/00
(52) U.S. Cl. ................................. 530/324; 514/12; 435/4
(58) Field of Search ............................... 530/324; 514/12; 435/4

(56) References Cited

U.S. PATENT DOCUMENTS 4,923,818    5/1990    Goldberg ............................ 435/320

FOREIGN PATENT DOCUMENTS

| 404750 | 12/1990 | (EP) | ............................... | C07K/15/06 |
| WO 90/11287 | 4/1990 | (WO) | ............................... | C07H/15/12 |

OTHER PUBLICATIONS

Hodgson, Biotechnology, vol. 13, pp. 554–557 (1995).
Stetler–Stevenson, et al; J. Biol. Chem. 264 (29), 17374–17378 (1989).
Goldberg et al., Proc. Natl. Acad. Sci. USA, 86, 8207–8211 (1989).
Willenbrock et al; Biochemistry 32 pp. 4330–4337 (1993).
Libson et al; Nature, Structural Biology, vol. 2 (11), pp. 938–942 (1995).
Strongin et al; J. Biol. Chem. 270 (10), 5331–5338 (1995).
Karelina et al; J. Invest. Dermatol. (105) (3), 411–417 (1995).
Rockwell et al; J. Am. Chem. Soc. 118 pp. 10337–10338 (1996).
Fridman, et al., J. Biol. Chem. 267(22), 15398–15405 (1992).
Gholke, et al., FEBS Lett. 378(2), 126–130 (1996).

*Primary Examiner*—Christopher S. F. Low
*Assistant Examiner*—David Lukton
(74) *Attorney, Agent, or Firm*—Scott J. Meyer

(57) ABSTRACT

Disclosed are a peptide and its use in a method of screening test compounds as potential inhibitors of matrix metalloproteinases. The peptide consists of residues Trp 574 to Asp 656 in the TIMP-2 binding site of the C-terminal domain of gelatinase-A as shown by SEQ ID NO:19. The method comprises determining the inhibitory effect of a test compound in a competitive inhibition assay with said peptide in which a Ki/Kd=>1 is deemed an inhibitory effect of said test compound, and in which Ki is the inhibitor constant of said test compound and Kd is the dissociation constant of said peptide.

2 Claims, 7 Drawing Sheets

Figure 1A:
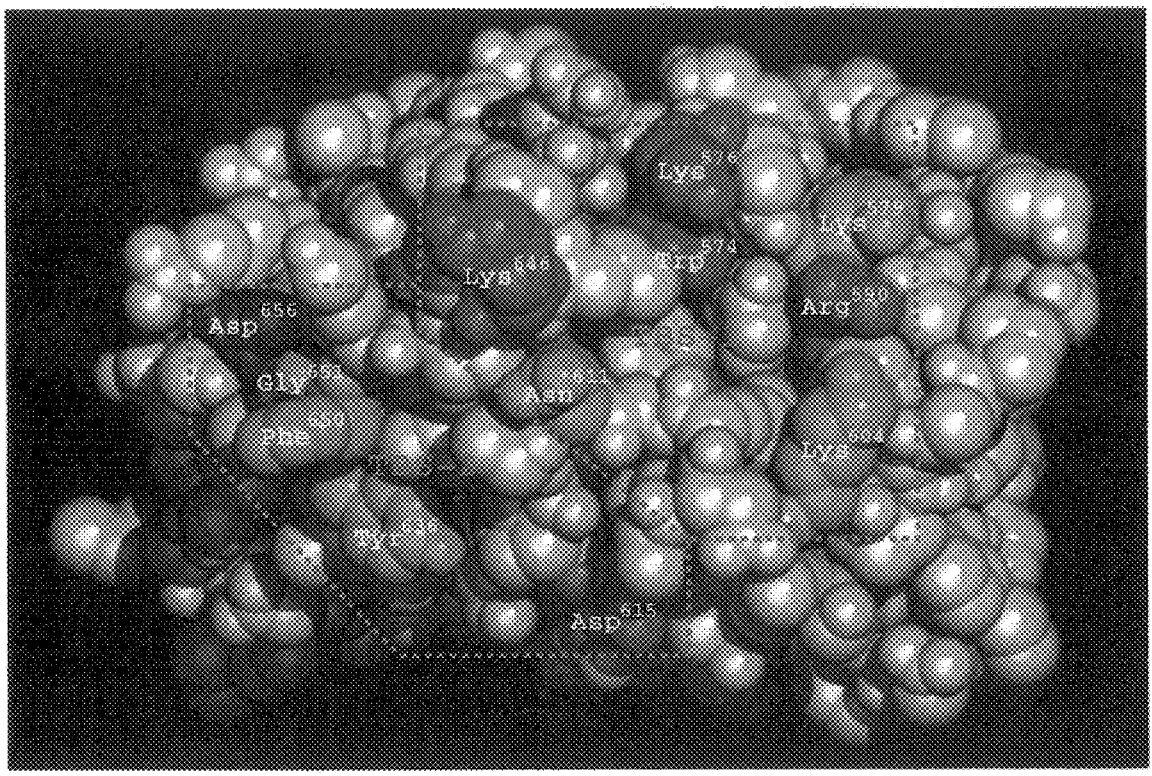

(4 of 7 Drawing Sheet(s) Filed in Color)

```
                          Blade III
            *   *                                           *
Gel A    573..NWSKNKKTYI FAGDKFWRYN EVKKKMDPGF PKLIADAWNA IP-
Gel B    618..RSGRG-KMLL FSGRRLWRFD VKAQMVDPRS ASEVDRMFPG VPL
Cli-Pig  382..FEEDTGKTYF FVAHECWRYD EYKQSMDTGY PKMIAEEFPG IG-
Cli-Hum       SEENTGKTYF FVANKYWRYD EYKRSMDPSY PKMIAHDFPG IG-
Col-3         HFEDTGKTLL FSGNQVWRYD DTNHIMDKDY PRLIEEDFPG IG-
Str-1         SDKEKNKTYF FVEDKYWRFD EKRNSMEPG- PKQIAEDFPG ID-
Str-2         SDKEKKKTYF FAADKYWRFD ENSQSMEQGF PRLIADDFPG VE-
Str-3         WGPEKNKIYF FRGRDYWRFH PSTRRVDSPV PRR-ATDWRG VPS
MT-MMP        WMPNG-KTYF FRGNKYYRFN EELRAVDSEY PKNI-KVWEG IP- Blade IV
          *                                    *          **    *
Gel A    615..DNLDAVVD LQGGGHSYFF KGAYYLKLEN QS-LKSV-KFGS IKSDWLGC
Gel B    660..DTHDVFQY RE---KAYFC QDRFYWRVSS RSELNQVDQVGY VTYDILQC
Cli-Pig  424..NKVDAVF- -QKDGFLYFF HGTRQYQFDF KT-KRIL-TLQK A-NSWFNC
Cli-Hum       HKVDAVF- -MKDGFFYFF HGTRQYKFDP KT-KRII-TLQK A-NSWFNC
Col-3         DKVDAVY- -EKNGYIYFF NGPIQFEYSI WS-NRIV-RVMP A-NSILWC
Str-1         SKIDAVF- -EEFGFFYFF TGSSQLEFDP NA-KKVT-HTLK S-NSWLNC
Str-2         PKVDAVL- -QAFGFFYFF SGSSQFEFDP NA-RMVT-HILK S-NSWLHC
Str-3         E-IDAAFQ -DADGYAYFL RGRLYWKFDP VKVKALEGFPRL VGPDFFGC
MT-MMP        ESPRGSFM GSDEVFTYFY KGNKYWKFNN QKLKVEPGYPKS ALRDWMGC
```

FIG. 5

SEQUENCE LISTING (1) GENERAL INFORMATION:

(iii) NUMBER OF SEQUENCES: 19

(2) INFORMATION FOR SEQ ID NO: 1:

(i) SEQUENCE CHARACTERISTICS:
        (A) LENGTH: 42 amino acids
        (B) TYPE: amino acid
        (C) TOPOLOGY: linear (ii) MOLECULE TYPE: peptide (xi) SEQUENCE DESCRIPTION: SEQ ID NO: 1:

Asn Trp Ser Lys Asn Lys Lys Thr Tyr Ile Phe Ala Gly Asp Lys
           5                    10                15

Phe Trp Arg Tyr Asn Glu Val Lys Lys Lys Met Asp Pro Gly Phe
           20                   25                30

Pro Lys Leu Ile Ala Asp Ala Trp Asn Ala Ile Pro
           35                   40

(2) INFORMATION FOR SEQ ID NO: 2:

(i) SEQUENCE CHARACTERISTICS:
        (A) LENGTH: 42 amino acids
        (B) TYPE: amino acid
        (C) TOPOLOGY: linear (ii) MOLECULE TYPE: peptide (xi) SEQUENCE DESCRIPTION: SEQ ID:NO: 2:

```
Arg Ser Gly Arg Gly Lys Met Leu Leu Phe Ser Gly Arg Arg Leu
                 5                  10                 15

Trp Arg Phe Asp Val Lys Ala Gln Met Val Asp Pro Arg Ser Ala
                20                  25                 30

Ser Glu Val Asp Arg Met Phe Pro Gly Val Pro Leu
                35                  40
```

(2) INFORMATION FOR SEQ ID NO: 3:

(i) SEQUENCE CHARACTERISTICS:
        (A) LENGTH: 42 amino acids
        (B) TYPE: amino acid
        (C) TOPOLOGY: linear (ii) MOLECULE TYPE: peptide (xi) SEQUENCE DESCRIPTION: SEQ ID NO: 3:

```
Phe Glu Glu Asp Thr Gly Lys Thr Tyr Phe Phe Val Ala His Glu
                 5                  10                 15

Cys Trp Arg Tyr Asp Glu Tyr Lys Gln Ser Met Asp Thr Gly Tyr
                20                  25                 30

Pro Lys Met Ile Ala Glu Glu Phe Pro Gly Ile Gly
                35                  40
```

(2) INFORMATION FOR SEQ ID NO: 4:

(i) SEQUENCE CHARACTERISTICS:
        (A) LENGTH: 42 amino acids
        (B) TYPE: amino acid
        (C) TOPOLOGY: linear (ii) MOLECULE TYPE: peptide (xi) SEQUENCE DESCRIPTION: SEQ ID NO: 4:

```
Ser Glu Glu Asn Thr Gly Lys Thr Tyr Phe Phe Val Ala Asn Lys
                 5                  10                 15

Tyr Trp Arg Tyr Asp Glu Tyr Lys Arg Ser Met Asp Pro Ser Tyr
                20                  25                 30

Pro Lys Met Ile Ala His Asp Phe Pro Gly Ile Gly
                35                  40
```

(2) INFORMATION FOR SEQ ID NO: 5:

(i) SEQUENCE CHARACTERISTICS:
        (A) LENGTH: 42 amino acids
        (B) TYPE: amino acid
        (C) TOPOLOGY: linear (ii) MOLECULE TYPE: peptide (xi) SEQUENCE DESCRIPTION: SEQ ID NO: 5:

```
His Phe Glu Asp Thr Gly Lys Thr Leu Leu Phe Ser Gly Asn Gln
                 5                  10                 15

Val Trp Arg Tyr Asp Asp Thr Asn His Ile Met Asp Lys Asp Tyr
                20                  25                 30

Pro Arg Leu Ile Glu Glu Asp Phe Pro Gly Ile Gly
                35                  40
```

(2) INFORMATION FOR SEQ ID NO: 6:

(i) SEQUENCE CHARACTERISTICS:
        (A) LENGTH: 41 amino acids
        (B) TYPE: amino acid
        (C) TOPOLOGY: linear (ii) MOLECULE TYPE: peptide (xi) SEQUENCE DESCRIPTION: SEQ ID NO: 6:

Ser Asp Lys Glu Lys Asn Lys Thr Tyr Phe Phe Val Glu Asp Lys
                 5                  10                  15

Tyr Trp Arg Phe Asp Glu Lys Arg Asn Ser Met Glu Pro Gly Pro
                20                  25                  30

Lys Gln Ile Ala Glu Asp Phe Pro Gly Ile Asp
                35                  40

(2) INFORMATION FOR SEQ ID NO: 7:

(i) SEQUENCE CHARACTERISTICS:
            (A) LENGTH: 42 amino acids
            (B) TYPE: amino acid
            (C) TOPOLOGY: linear (ii) MOLECULE TYPE: peptide (xi) SEQUENCE DESCRIPTION: SEQ ID NO: 7:

Ser Asp Lys Glu Lys Lys Lys Thr Tyr Phe Phe Ala Ala Asp Lys
                 5                  10                  15

Tyr Trp Arg Phe Asp Glu Asn Ser Gln Ser Met Glu Gln Gly Phe
                20                  25                  30

Pro Arg Leu Ile Ala Asp Asp Phe Pro Gly Val Glu
                35                  40

(2) INFORMATION FOR SEQ ID NO: 8:

(i) SEQUENCE CHARACTERISTICS:
            (A) LENGTH: 42 amino acids
            (B) TYPE: amino acid
            (C) TOPOLOGY: linear (ii) MOLECULE TYPE: peptide (xi) SEQUENCE DESCRIPTION: SEQ ID NO: 8:

Trp Gly Pro Glu Lys Asn Lys Ile Tyr Phe Phe Arg Gly Arg Asp
                 5                  10                  15

Tyr Trp Arg Phe His Pro Ser Thr Arg Arg Val Asp Ser Pro Val
                20                  25                  30

Pro Arg Arg Ala Thr Asp Trp Arg Gly Val Pro Ser
                35                  40

(2) INFORMATION FOR SEQ ID NO: 9:

(i) SEQUENCE CHARACTERISTICS:
            (A) LENGTH: 40 amino acids
            (B) TYPE: amino acid
            (C) TOPOLOGY: linear (ii) MOLECULE TYPE: peptide (xi) SEQUENCE DESCRIPTION: SEQ ID NO: 9:

Trp Met Pro Asn Gly Lys Thr Tyr Phe Phe Arg Gly Asn Lys Tyr
                 5                  10                  15

Tyr Arg Phe Asn Glu Glu Leu Arg Ala Val Asp Ser Glu Tyr Pro
                20                  25                  30

Lys Asn Ile Lys Val Trp Glu Gly Ile Pro
                35                  40

(2) INFORMATION FOR SEQ ID NO: 10:

(i) SEQUENCE CHARACTERISTICS:
    (A) LENGTH: 46
    (B) TYPE: amino acid
    (C) TOPOLOGY: linear (ii) MOLECULE TYPE: peptide (xi) SEQUENCE DESCRIPTION: SEQ ID NO: 10:

Asp Asn Leu Asp Ala Val Val Asp Leu Gln Gly Gly Gly His Ser
                 5                  10                 15

Tyr Phe Phe Lys Glu Ala Tyr Tyr Leu Lys Leu Glu Asn Gln Ser
                20                  25                 30

Leu Lys Ser Val Lys Phe Gly Ser Ile Lys Ser Asp Trp Leu Gly
                35                  40                 45

Cys (2) INFORMATION FOR SEQ ID NO: 11:

(i) SEQUENCE CHARACTERISTICS:
        (A) LENGTH: 45 amino acids
        (B) TYPE: amino acid
        (C) TOPOLOGY: linear (ii) MOLECULE TYPE: peptide (xi) SEQUENCE DESCRIPTION: SEQ ID NO: 11:

Asp Thr His Asp Val Phe Gln Tyr Arg Glu Lys Ala Tyr Phe Cys
                 5                  10                 15

Gln Asp Arg Phe Tyr Trp Arg Val Ser Ser Arg Ser Glu Leu Asn
                20                  25                 30

Gln Val Asp Gln Val Gly Tyr Val Thr Tyr Asp Ile Leu Gln Cys
                35                  40                 45

(2) INFORMATION FOR SEQ ID NO: 12:

(i) SEQUENCE CHARACTERISTICS:
        (A) LENGTH: 43 amino acids
        (B) TYPE: amino acid
        (C) TOPOLOGY: linear (ii) MOLECULE TYPE: peptide (xi) SEQUENCE DESCRIPTION: SEQ ID NO: 12:

Asn Lys Val Asp Ala Val Phe Gln Lys Asp Gly Phe Leu Tyr Phe
                 5                  10                 15

Phe His Gly Thr Arg Gln Tyr Gln Phe Asp Phe Lys Thr Lys Arg
                20                  25                 30

Ile Leu Thr Leu Gln Lys Ala Asn Ser Trp Phe Asn Cys
                35                  40

(2) INFORMATION FOR SEQ ID NO: 13:

(i) SEQUENCE CHARACTERISTICS:
        (A) LENGTH: 43 amino acids
        (B) TYPE: amino acid
        (C) TOPOLOGY: linear (ii) MOLECULE TYPE: peptide (xi) SEQUENCE DESCRIPTION: SEQ ID NO: 13:

His Lys Val Asp Ala Val Phe Met Lys Asp Gly Phe Phe Tyr Phe
                 5                  10                 15

Phe His Gly Thr Arg Gln Tyr Lys Phe Asp Pro Lys Thr Lys Arg
                20                  25                 30

Ile Ile Thr Leu Gln Lys Ala Asn Ser Trp Phe Asn Cys
            35                  40

(2) INFORMATION FOR SEQ ID NO: 14:

(i) SEQUENCE CHARACTERISTICS:
        (A) LENGTH: 43 amino acids
        (B) TYPE: amino acid
        (C) TOPOLOGY: linear (ii) MOLECULE TYPE: peptide (xi) SEQUENCE DESCRIPTION: SEQ ID NO: 14:

Asp Lys Val Asp Ala Val Tyr Glu Lys Asn Gly Tyr Ile Tyr Phe
                5                  10                  15

Phe Asn Gly Pro Ile Gln Phe Glu Tyr Ser Ile Trp Ser Asn Arg
                20                 25                  30

Ile Val Arg Val Met Pro Ala Asn Ser Ile Leu Trp Cys
            35                  40

(2) INFORMATION FOR SEQ ID NO: 15:

(i) SEQUENCE CHARACTERISTICS:
        (A) LENGTH: 43 amino acids
        (B) TYPE: amino acid
        (C) TOPOLOGY: linear (ii) MOLECULE TYPE: peptide (xi) SEQUENCE DESCRIPTION: SEQ ID NO: 15:

Ser Lys Ile Asp Ala Val Phe Glu Glu Phe Gly Phe Phe Tyr Phe
                5                  10                  15

Phe Thr Gly Ser Ser Gln Leu Glu Phe Asp Pro Asn Ala Lys Lys
                20                 25                  30

Val Thr His Thr Leu Lys Ser Asn Ser Trp Leu Asn Cys
            35                  40

(2) INFORMATION FOR SEQ ID NO: 16:

(i) SEQUENCE CHARACTERISTICS:
        (A) LENGTH: 43 amino acids
        (B) TYPE: amino acid
        (C) TOPOLOGY: linear (ii) MOLECULE TYPE: peptide (xi) SEQUENCE DESCRIPTION: SEQ ID NO: 16:

Pro Lys Val Asp Ala Val Leu Gln Ala Phe Gly Phe Phe Tyr Phe
                5                  10                  15

Phe Ser Gly Ser Ser Gln Phe Glu Phe Asp Pro Asn Ala Arg Met
                20                 25                  30

Val Thr His Ile Leu Lys Ser Asn Ser Trp Leu His Cys
            35                  40

(2) INFORMATION FOR SEQ ID NO: 17:

(i) SEQUENCE CHARACTERISTICS:
        (A) LENGTH: 46 amino acids
        (B) TYPE: amino acid
        (C) TOPOLOGY: linear (ii) MOLECULE TYPE: peptide (xi) SEQUENCE DESCRIPTION: SEQ ID NO: 17:

-continued

```
Glu Ile Asp Ala Ala Phe Gln Asp Ala Asp Gly Tyr Ala Tyr Phe
              5                  10                  15

Leu Arg Gly Arg Leu Tyr Trp Lys Phe Asp Pro Val Lys Val Lys
              20                  25                  30

Ala Leu Glu Gly Phe Pro Arg Leu Val Gly Pro Asp Phe Phe Gly
              35                  40                  45

Cys
```

(2) INFORMATION FOR SEQ ID NO: 18:

(i) SEQUENCE CHARACTERISTICS:
        (A) LENGTH: 48 amino acids
        (B) TYPE: amino acid
        (C) TOPOLOGY: linear (ii) MOLECULE TYPE: peptide (xi) SEQUENCE DESCRIPTION: SEQ ID NO: 18:

```
Glu Ser Pro Arg Gly Ser Phe Met Gly Ser Asp Glu Val Phe Thr
              5                  10                  15

Tyr Phe Tyr Lys Glu Asn Lys Tyr Trp Lys Phe Asn Asn Gln Lys
              20                  25                  30

Leu Lys Val Glu Pro Gly Tyr Pro Lys Ser Ala Leu Arg Asp Trp
              35                  40                  45

Met Gly Cys
```

(2) INFORMATION FOR SEQ ID NO: 19:

(i) SEQUENCE CHARACTERISTICS:
        (A) LENGTH: 83 amino acids
        (B) TYPE: amino acid
        (C) TOPOLOGY: linear (ii) MOLECULE TYPE: peptide (xi) SEQUENCE DESCRIPTION: SEQ ID NO: 19:

```
Trp Ser Lys Asn Lys Lys Thr Tyr Ile Phe Ala Gly Asp Lys Phe
              5                  10                  15

Trp Arg Tyr Asn Glu Val Lys Lys Lys Met Asp Pro Gly Phe Pro
              20                  25                  30

Lys Leu Ile Ala Asp Ala Trp Asn Ala Ile Pro Asp Asn Leu Asp
              35                  40                  45

Ala Val Val Asp Leu Gln Gly Gly Gly His Ser Tyr Phe Phe Lys
              50                  55                  60

Glu Ala Tyr Tyr Leu Lys Leu Glu Asn Gln Ser Leu Lys Ser Val
              65                  70                  75

Lys Phe Gly Ser Ile Lys Ser Asp
              80
```

METHOD OF CELL SURFACE ACTIVATION AND INHIBITION

This is a division of application Ser. No. 08/942,330, filed Sep. 5, 1997, now U.S. Pat. No. 6,022,948 which is a continuation of application Ser. No. 60/026,226, filed Sep. 17, 1996.

FIELD AND OBJECTIVE OF THE INVENTION

This invention relates to methods for cell surface activation and inhibition. More particularly, the invention relates to methods of cell surface activation and inhibition that involve the interaction of an inhibitor of matrix metalloprotease known as TIMP-2, with the enzyme, gelatinase-A.

Matrix metalloproteases (MMPs) are ubiquitous in human disease and development. Most processes that involve a certain amount of tissue repair and damage are believed to be influenced by MMPs such as, for example, in degradation of type IV collagen that might occur in rheumatoid or osteoarthritis and remodeling of endothelial walls in restenosis. MMPs are also implicated in various aspects of cancer such as primary tumor formation, metastasis, and the vascularization of larger tumors (angiogenesis). It is also known that MMPs are involved in the conversion of inactive tumor necrosis factor (TNF) precursor into active TNF, which in turn is implicated in rheumatoid arthritis, Crohn's disease, multiple sclerosis, cachexia and sepsis.

Consequently, the screening for MMP inhibitors as potential drugs is of significant use in the medical and pharmaceutical fields.

MMPs are secreted by mammalian cells as zymogens and upon activation initiate tissue remodeling by proteolytic degradation of collagens and proteoglycans. Activation of the secreted proenzymes and interaction with their specific inhibitors, TIMP-1 and TIMP-2, determine the net enzymatic activity in the extracellular space.

TIMP-2 forms a specific complex with the proform of gelatinase-A (GelA) which is mediated by interaction with the C-terminal domain (GelA-CTD) of the enzyme. The amino acid sequence of the 72 kDa GelA is disclosed in Goldberg, U.S. Pat. No. 4,923,818, and its complex with TIMP-2 is disclosed in Goldberg published European Patent Application, EP 404,750. GelA is a multi-domain protein containing a catalytic domain, a domain with three type II fibronectin-like repeats, and a C-terminal domain.

Soluble GelA proenzyme is recruited to the cell surface where it is specifically activated by MT1-MMP, a membrane bound metalloprotease. The binding of GelA to cell surface and its subsequent activation is also mediated by GelA-CTD. Consequently, cell surface activation is inhibited in the presence of exogenously added excess of TIMP-2 or recombinant GelA-CTD.

It has not been known previously how the MT1-MMP that is inhibited by complex with TIMP-2 is able to cleave the GelA propeptide to initiate activation of the pro-enzyme. Resolution of this question is critical to an understanding of the mechanism by which GelA-CTD interacts with TIMP-2 and MT1-MMP on the cell surface.

BACKGROUND OF THE INVENTION

Literature references on the following background information and on conventional test method and laboratory procedures well known to the ordinary person skilled in the art, and other such state-of-the-art techniques as used herein, are indicated in parentheses, and appended at the end of the specification.

Secreted metalloproteases (MMPs) initiate tissue remodeling by degradation of extracellular matrix (ECM) macromolecules (reviewed in 1–3). Normal physiological processes such as morphogenesis, tissue repair, and angiogenesis, are dependent upon spatial and temporal regulation of the activity of these enzymes, while malignant cells exploit these same proteases to promote invasion and metastasis (4–7). A clear understanding of the mechanisms governing regulation of MMP activity in extracellular space has remained an elusive goal. The MT1-MMP/GelA system (8–16) provides a first glimpse at a mechanism by which an activity of a soluble MMP, GelA (17), can be spatially regulated via its recruitment to the cell surface where the GelA proenzyme is converted into its active form. Transfection of Cos1 cells with MT1-MMP is sufficient to cause GelA binding to the cell surface and its activation (8,19). The cell surface activation of GelA involves a two step proteolytic processing of its propeptide. The first cleavage of the $Asn^{37}$-Leu peptide bond is dependant on MT1-MMP (9), a membrane bound metalloprotease. This cleavage is also dependent on GelA having an intact C-terminal domain since a truncated form of the GCLA proenzyme lacking a C-terminal domain can not be activated by membrane bound MT1-MMP (13). Consequently the exogenously added recombinant GelA-CTD) is a competitive inhibitor of $Asn^{37}$-Leu cleavage (9,10). Finally this reaction is inhibited in the presence of an excess of inhibitor, TIMP-2, while TIMP-1 has no effect. The consequent cleavage of propeptide is accomplished via an autoproteolytic, MT1-MMP independent mechanism (9,10,1 8,19) to generate a 62 kDa active GelA with an amino-terminal residue $Tyr^{81}$. These data demonstrate that binding of GelA to the cell surface via its CTD is a prerequisite for enzyme activation. We have previously shown that two closely related proenzymes GelA and B form specific complexes with TIMP-2 and TIMP-1 respectively (20). These complexes are also formed via inhibitor interaction with the carboxyl-end domain of proenzyme (21,22). Thus TIMP-2 and cell surface binding activities of GelA-CTD appear to be interrelated. We have purified activated form of MT1-MMP using affinity chromatography approach (9) and demonstrated that it acts as cell surface TIMP-2 receptor with $Kd=1.65\times10^{-9}M$. The MT1-MMP-TIMP-2 complex in turn acts as a receptor for GelA-CTD ($Kd=0.42\times10^{-9}M$). The data we have presented support the hypothesis that the cell surface binding of GelA-CTD occurs via formation of a tri-molecular complex of activated MT1-MMP/TIMP-2/pro-GelA that promotes pro-GelA activation. This model, however, does not satisfactory resolve the GelA activation mechanism for the following reasons. The inhibitor TIMP-2 consists of two domains. The amino-terminal, inhibitory domain interacts with the active center of MMPs to form an inhibitory complex (23,24). The C-terminal domain binds to GelA-CTD. Thus the inhibitory complex of TIMP-2 with activated MT1-MMP can leave the C-terminal domain of the inhibitor exposed and available for interaction with GelA-CTD. In fact we have reported an analogous tri-molecular complex between GelB, TIMP-1 and activated interstitial collagens (22) where the collagens component of the complex was inhibited. Moreover the specific inhibition of soluble form of MT1-MMP by TIMP-2 has been recently demonstrated (25,26). Thus, the model of cell surface GelA activation that requires assembly of the MT1-MMP/TIMP-2/pro-GelA complex leaves unanswered the question of how the MT1-MMP inhibited by TIMP-2 is able to cleave the $Asn^{37}$-Leu peptide bond to initiate activation of the pro-enzyme. An answer to this question demands a better understanding of the mechanism by which GelA-CTD interacts with TIMP-2 and MT1-MMP on the cell surface. We have recently reported the high resolution crystal structure of GelA-CTD (27). Here we report the results of extensive alanine scanning mutagenesis of solvent exposed GelA-CTD amino-acid residues and, using the coordinates of the GelA-CTD structure, define a TIMP-2 binding site on the surface of this domain. By comparison of the TIMP-2 binding site to the same regions in related MMP structures, we characterize structural features required for general TIMP binding and the specificity of TIMP-2- GelA-CTD interaction. We also report analysis of GelA activation inhibition activity of GelA-CTD mutants relative to that of wild type.

BRIEF DESCRIPTION OF THE INVENTION

In accordance with the present invention, methods of cell surface activation and inhibition are provided which are useful for the screening of MMP inhibitors that are potentially useful for the treatment of diseases that involve tissue repair and damage and other diseases in which MMPs are implicated.

Critical to the methods of the invention is the discovery of a unique portion of the TIMP-2 binding site on the surface of the GelA-CTD domain, which has been determined herein to be the very strongly binding residue $Asp^{656}$. This critical TIMP-2 binding site can also include other residues in the GelA-CTD domain with which $Asp^{656}$ forms a contiguous surface, namely the less strongly binding residues $Gly^{651}$, $Phe^{650}$, and $Tyr^{636}$.

In accordance with another embodiment of the invention, the TIMP-2 binding site includes the foregoing four residues and additionally the very strongly binding residues $Asp^{615}$, $Lys^{646}$, $Lys^{576}$, $Trp^{574}$, and $Arg^{590}$, and the less strongly binding residues $Lys^{579}$, $Lys^{604}$ and $Asn^{611}$. The effect of these residues on the TIMP-2 binding of GelA-CTD has been confirmed by mutagenesis.

Point mutations can be made at these residues in the TIMP-2 binding site to impact the TIMP-2 binding to GelA-CTD, e.g., to inhibit or retard the binding, and thereby provide a unique screening method.

Identification of this TIMP-2 binding site provides a useful target for the screening of MMP inhibitors and for the prognosis and treatment of diseases in which MMPs are implicated. Compounds which are structured to competitively inhibit cell surface activation can be candidate MMP inhibitors.

DETAILED DESCRIPTION OF THE INVENTION

The following description of the invention taken in conjunction with the accompanying drawings is provided to further illustrate the invention and preferred embodiments in greater detail.

BRIEF DESCRIPTION OF THE DRAWINGS

The file of this patent contains at least one drawing executed in color. Copies of this patent with color drawings (s) will be provided by the Patent and Trademark Office upon request and payment of the necessary fee.

Figure Legends.

FIG. 1A and B. Space-filling model (A, 34) and ribbon diagram (B, 35) of Gel A-Ctd showing residues which interact with TIMP-2. A) The residues which are thought to directly interact with TIMP-2 are shown colored and labeled. Residues which showed between a 2- to 100-fold loss in TIMP-2 binding when mutated to alanine are colored cyan, while those which showed over 100-fold loss in TIMP-2 binding when mutated to alanine are colored dark blue. TBS-1 and TBS-2 regions are indicated by the dashed magenta boxes which cover their respective regions. B) A ribbon diagram of Gel A-Ctd shows the canonical β-propeller fold. Each blade of Gel A-Ctd is labeled with a roman numeral. The Ca2+ ion is shown in red along the central axis of symmetry. The disulfide bond connecting blades I and IV is shown as are the N- and C- termini. Residues which are thought to directly interact with TIMP-2 are shown in magenta and are labeled. All the residues lie on blade III, blade IV or the loop connecting the two blades.

FIG. 2. Competition Assay of GelA-Ctd Binding to TIMP-2. One hundred μL of solution containing $1.7\times10^{-9}$M of $^{125}$ I-labeled WT GelA-Ctd ($10^8$ cpm/μg) and unlabeled purified recombinant WT or mutant of the GelA-Ctd at the indicated concentrations were incubated in TIMP-2 (50 ng) coated wells of microtiter plates and washed as described in Methods. Bound radioactivity was determined by counting individual wells in a gamma counter. After background substraction the CPM retained in the wells was normalized to 1.00 and plotted versus the concentration of unlabeled, competing Gel A-Ctd for wild type (◇, Ki/Kd=1) or mutants $Gly^{651}$ (X, Ki/Kd=3); $Lys^{579}$ (□, Ki/Kd=6); $Lys^{604}$ (Δ, Ki/Kd=25); and $Asp^{615}$ (○, Ki/Kd=300) as indicated in the figure. The values for wild type self competition are the mean of 8 separate experiments and the error bars represent the standard error. The mutant values are the average of two determinations. Computer generated theoretical curves were fitted to the data and the apparent Kd for WT and Ki for mutants were determined from the fit as shown in the figure by each solid curve.

FIG. 3. Molecular surface of Gel A-Ctd showing the TIMP-2 binding site. A molecular surface of Gel A-Ctd was calculated and displayed using GRASP. The TIMP-2 binding site is colored magenta. The yellow labels denote some of the TIMP-2 binding residues and their position with respect to the surface. The boundary residues described in the paper are shown in green and are seen to surround the TIMP-2 binding site.

FIG. 4. Comparison of molecular surface and electrostatic potential at surface of Gel A-Ctd and CII-Ctd). The molecular surface of both (4A) Gel A-Ctd and (4B) CII-Ctd are displayed. Electrostatic potential for each was calculated and displayed with positive potential shown in blue and negative potential in red. The dashed magenta line conforms to the approximate TIMP-2 binding site described in the text. TBS-1 and TBS-2 are shown and conform to the same regions described in FIG. 1. The TBS-1 region of Gel A-Ctd displays a lot of positive potential, where as CII-Ctd has much less positive potential and has a significant amount of negative potential across the TBS-1 binding interface. The TBS-2 regions of both molecules show differing potentials as well. The molecular surfaces of both molecules suggests that they would present significantly different van der Waal contact surfaces.

FIG. 5. Sequence alignment of β-propeller blades III and IV from C-terminal domains of MMP family members. The amino acid sequence of GelA containing all the residues defining the TIMP-2 binding site was aligned with other MMPs. Sequences which are found in blade III or blade IV are beneath the underlined regions. GelA residues which are part of the TIMP-2 binding site and corresponding residues from other enzymes are bolded. Those residues constituting the TBS-1 region (see text) are bolded and underlined, while the remaining residues are part of TBS-2 are merely bolded.

An '*' marks residues whose effect on TIMP-2 binding of GelA-CTD were confirmed by mutagenesis. The residues defining the TIMP-2 binding site are thus shown to comprise the peptide from the first * to the last * in the GelA-CTD, namely, $Trp^{574}$ to $Asp^{65}$.

Figure 6:
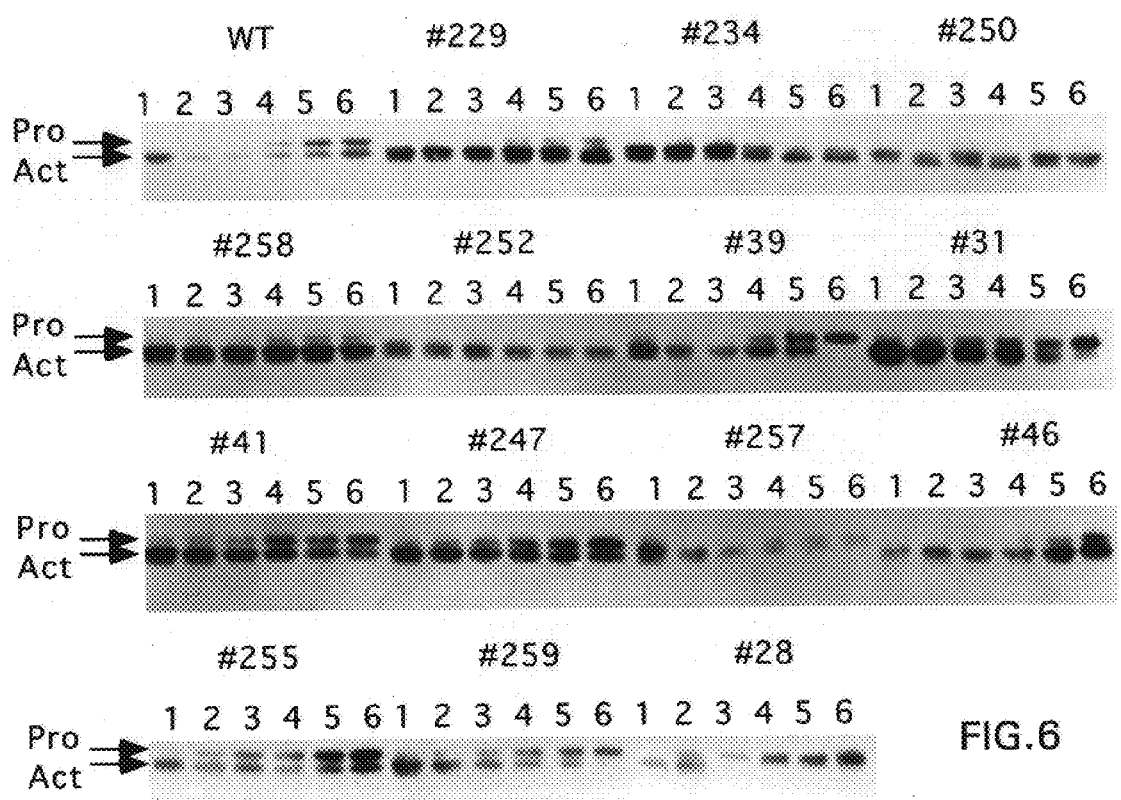

FIG. 6. Inhibition of membrane dependent activation of GelA by GelA-CTD mutants. The 15 ng of purified GelA were incubated in 25 mM HEPES-KOH buffer, pH 7.5, containing 0.1 mM $CaCl_2$ with 20 μg of plasma membrane protein from HT1080 cells for 2 h at 370° C. in the presence of increasing concentration (1–6) of recombinant GelA-CTD WT or mutants #28 ($Asp^{569}$), #31 ($Lys^{579}$), #39 ($Lys^{604}$), #41 ($Asp^{615}$), #229 ($Asp^{576}$), #234 ($Arg^{590}$), #247 ($Lys^{646}$), #250 ($Trp^{574}$), #252 ($Tyr^{636}$), #255 ($Phe^{650}$), #257 ($Gly^{651}$), #258 ($Asp^{656}$), #259 ($Asn^{611}$) as indicated in each panel. The results of activation reaction were analyzed on zymogram as described previously (9,10). The images of resulting zymograms were acquired using flat bed scanner and converted to a negative.

Figure 3:
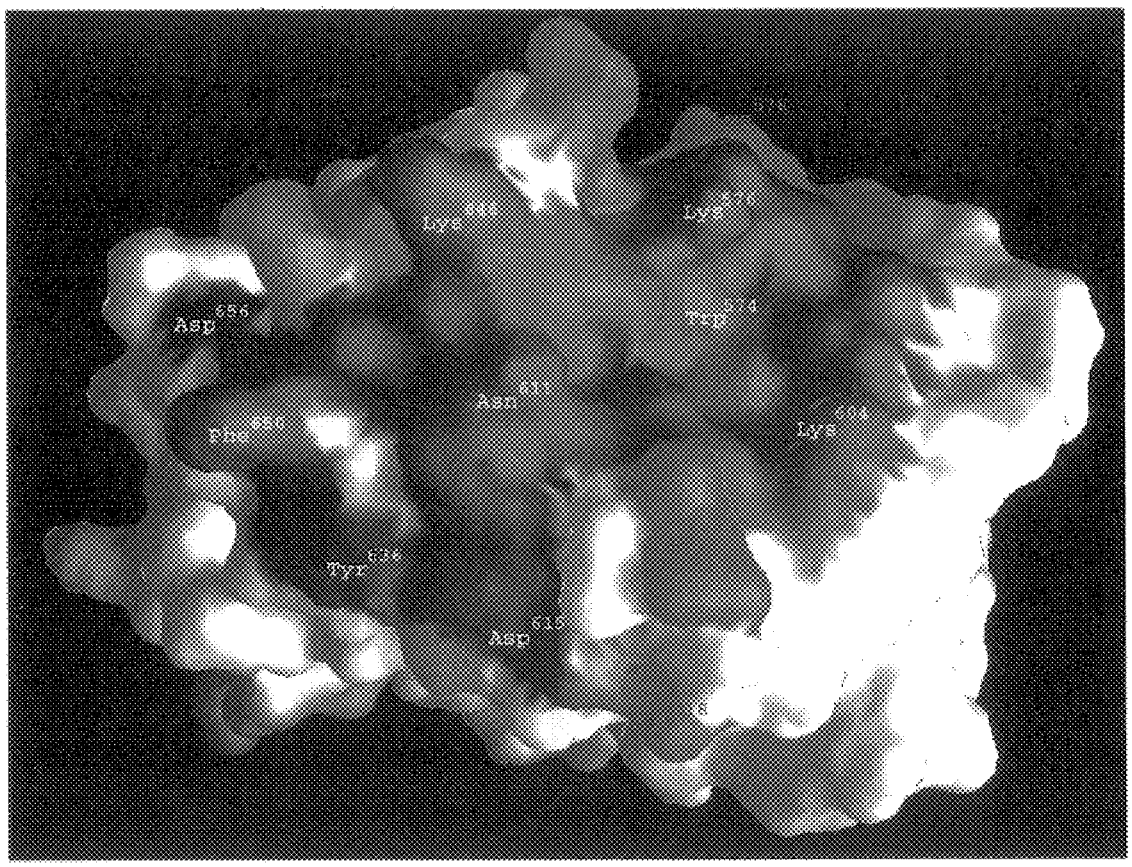

The colored areas in FIG. 1A and FIG. 3 are shown in black and white copies as follows:

FIG. 1A—Residues shown in dark blue are $Asp^{656}$, $Asp^{615}$, $Lys^{646}$, $Lys^{576}$, $Trp^{574}$ and $Arg^{590}$. Residues shown in cyan are $Gly^{651}$, $Phe^{650}$, $Tyr^{636}$, $Asn^{611}$, $Lys^{579}$ and $Lys^{604}$.

FIG. 3—Boundary residues shown in the green colored area are $Lys^{649}$, $Gln^{641}Lys^{578}$, $Lys^{633}$, $Asp^{608}$ and $Asp^{618}$. The red colored TIMP-2 binding site shows residues $Asp^{656}$, $Phe^{650}$, $Tyr^{636}$, $Asp^{615}$, $Asn^{611}$, $Lys^{646}$, $Lys^{576}$, $Trp^{574}$ and $Lys^{604}$.

In order to further illustrate the invention, the following detailed examples were carried out although it will be understood that the invention is not limited to these examples or the details described therein.

EXAMPLES

Materials and Methods

Cell Culture.

HT1080 fibrosarcoma cells were grown in monolayer culture in RPMI 1640 media supplemented with 4% fetal calf serum and 2 mM glutamine in the presence of 5% $CO_2$ and treated with 12-O-tetradecanoyl-phorbol acetate (TPA) (50 ng/ml for 16 h). Isolation of plasma membranes from HT1080 cells was performed using discontinuous sucrose gradient as described (9,10).

Enzyme Purification.

The GelA expression plasmid p6R72hyg was transfected into E1A-expressing p2AHT2a cells and GelA was purified from conditioned medium of stably transfected cell line p2AHT7212A as described (9,10)

Expression and Purification of TIM P-2.

Recombinant TIMP-2 was expressed in p2AHT2a cells transfected with TIMP-2 cDNA in the p6Rhyg expression vector and purified from serum free conditioned media of p2AHT2aT2 cells as described earlier (9,10) using Reactive Red-120-Agarose (Sigma, R-0503), Q-Sepharose (Pharmacia #17-0510-01), CM-Sepharose CL-6B (Sigma #CCL-6B-100) and RP-HPLC column chromatography.

Expression and Purification of the FLAG GelA-CTD Fusion Protein.

Expression vector pFLAG72CT was constructed by cloning a fragment from GelA cDNA (17) coding for $Leu^{444}$-$Cys^{660}$ into E.Coli secretion vector pFlag1 (IBI Inc.). The resulting vector coding for the fusion protein FLAG-CT was transfected into an E.coli TOPP5 host (Stratagene). Protein was purified from a periplasmic fraction by chromatography on Reactive Red-120-Agarose (Sigma, R-0503) and M1 anti-flag antibody affinity column as described previously (9,10,27). Each of the 50 mutants and wild type GelA CT were purified using this procedure.

Mutagenesis of the FLAG GelA-CTD Fusion Protein.

Expression vector pFLAG72CT was mutagenized directly using PCR mediated site directed mutagenesis. A pair of anti-parallel 33 base pair long primers was synthesized for each mutant. These primers containing a desired mutation were used in a pair of PCR reactions with either of two primers flanking the coding sequence. Both resulting PCR products contained mutation. They were mixed, melted and annealed to generate a partial heteroduplex encompassing the whole coding sequence. The latter served as a template in a third PCR reaction primed by both of the flanking primers. Each of the resulting PCR products was cloned back into the pFLAG72CT expression vector and subjected to a sequence analysis to confirm the presence of mutation. All resulting mutant proteins were purified and assayed for TIMP-2 binding as described below. The sequence of mutants that had negative effect on TIMP-2 binding was verified by sequencing of the entire coding region to exclude the appearance of secondary, PCR generated, mutations. Secondary mutations, when present, were separated from the desired mutant by either a second round of PCR or using restriction enzyme mediated subcloning.

TIMP-2 binding of the FLAG-GelA-CTD Fusion Protein.

The TIMP-2 binding and competition assays were performed in 96 well modular plates (Costar). TIMP-2 coated plates were prepared by addition of 100 μl of loading buffer (20 mM Tris HCl, pH 9) containing 50 ng of purified TIMP-2 to each well and incubated for 1 h at RT. This solution was replaced with 200 μl of blocking buffer (0.5% BSA and 0.02% Brij in PBS, pH 7.2) and incubated ON at 4° C. For binding experiments increasing concentrations of competing cold ligand in 100 μl of binding buffer (1 mg/ml BSA and 0.01% Brij in PBS) were added to TIMP-2 or BSA (control) coated wells and incubated for 30 min prior to addition of $10^{-9}$M of $^{125}$I-GelA-CTD (between $6,5 \times 10^7$ and $1 \times 10^8$ dpm/μg). Incubation continued for 1 h, after which plates were washed 5 times with Binding Buffer and each well was counted to determine retained radioactivity.

Activation of the GelA Proenzyme.

Between 15–50 ng of the GelA proenzyme was used for activation with plasma membranes (1–4 μg of plasma membrane protein) in 10 μl final volume of 25 mM HEPES-KOH buffer, pH 7.5, containing 0.1 mM $CaCl_2$. The reaction was incubated at 37° C. for 120 min, terminated by addition of the sample buffer and subjected to gelatin zymogram analysis as described (9,10).

Protein Structure Analysis.

Residues whose mutation to alanine caused a loss in TIMP-2 binding were divided into those that most likely directly interact with TIMP-2 and those whose effect on TIMP-2 binding arc most likely a result of indirect structural perturbations based on a detailed examination of the environment of each of the mutant. The set of residues which interact with TIMP-2 are all confined to a single, contiguous surface of GelA-CTD which is divided into two adjacent regions, TBS1 and TBS2. Using boundary residues which are near the TIMP-2 binding residues but whose mutation to alanine had no effect on TIMP-2 binding permitted us to defined the TIMP-2 binding site as a molecular surface that includes residues not mutated in the analysis.

GelA-CTD and the C-terminal domain of interstitial collagens (ClI-Ctd) were aligned along their respective $C_\alpha$ atoms. The two structures aligned with an average root mean square difference in $C_\alpha$ position of 3.7 Å and were visualized using the graphics program O (28). The model of GelB-CTD was constructed using the modeling software, Sybyl (version 6.2, Tripos Associates, St. Louis, Mo.). The GelA-CTD structure provided the basic template for the structure and the coordinates of the $C_\alpha$ atoms were preserved in regions of sequence identity. In these regions, the conformation of the sidechains were preserved as well. In regions with no sequence identity, the $C_\alpha$ positions were held constant but the side chain conformation was chosen from a rotamer library set. Steric clashes due to the insertion of GelB residues were relieved by moving either the neighboring atoms (whether they be sidechains or backbone atoms) or by moving the $C_\alpha$ position of the substituted residue. Regions requiring the insertion or deletion of residues in the sequence only occurred along loops or turns and were modeled by choosing a turn or loop from the Brookhaven protein data bank that had a similar sequence and made the fewest van der Waal contacts with nearby atoms. Finally, the model was completed by minimizing van der Waal contacts over the entire structure. The final GelB-CTD model was aligned with GelA-CTD along their respective $C_\alpha$ atoms.
Results.

Description of GelA-CTD Structure

Figure 1B:
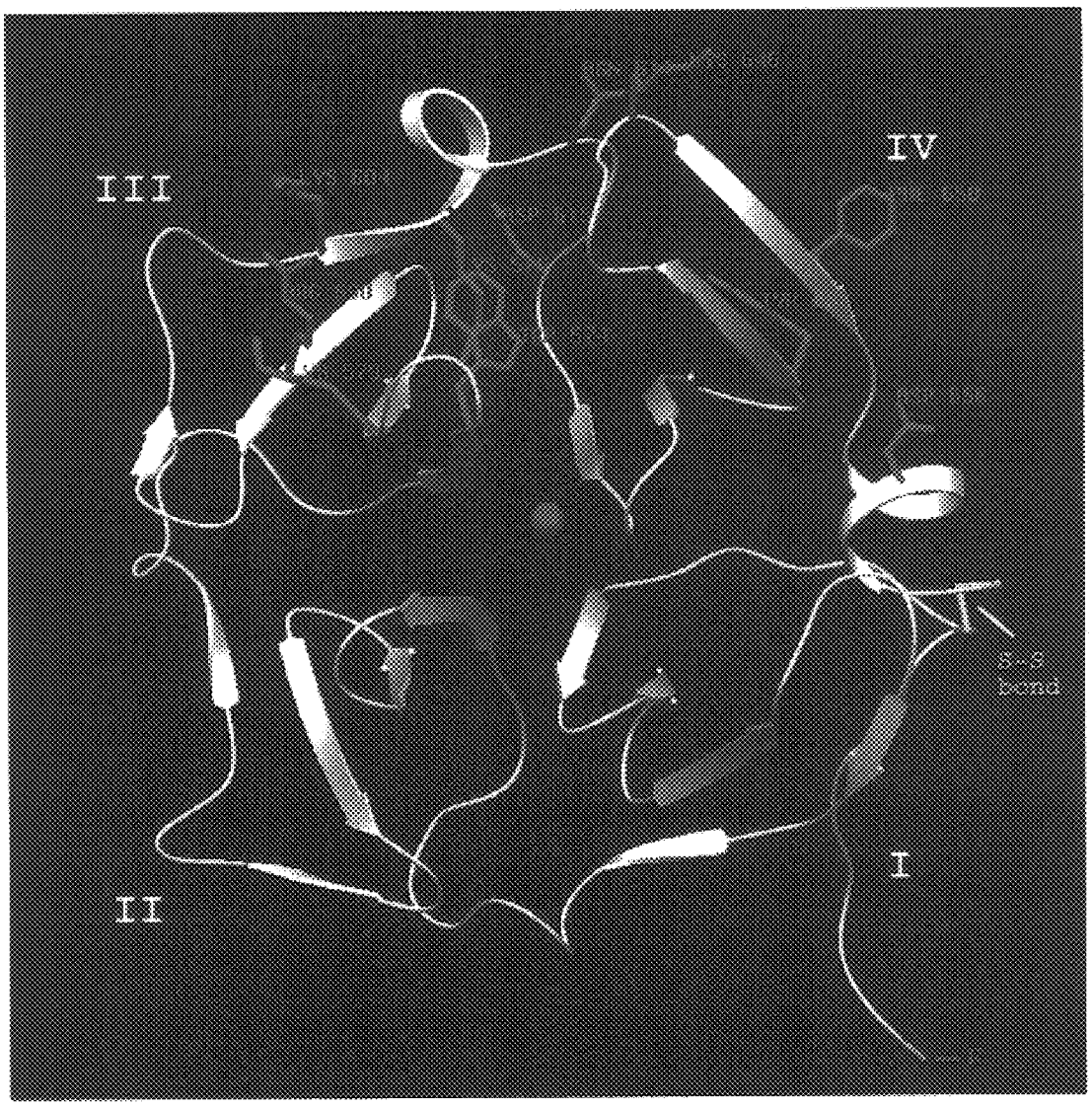

The GelA-CITD coordinates are from a high resolution crystal structure (resolution=2.15 Å) with a low R-factor (18.8%) and low average coordinate error (<0.25 Å) (27), so the positions of the backbone and sidechain atoms are well determined. The structure includes all residues between $Leu^{461}$ and $Cys^{660}$ where the only residues with poorly defined positions are $Glu^{529}$ and $Glu^{530}$. The overall structure of GelA-CTD is best described as a four-bladed β-propeller (FIG. 1). The four 'blades' are each composed of four strands of anti-parallel P-sheet. The β-sheet domains are twisted making the fourth, outer most strand form nearly an 80° angle with the inner most strand. Each blade is arrayed about a central pseudo four-fold axis so that a 90° rotation about the axis positions one blade on top of another. A channel formed by the four blades, parallel to the rotation axis, contains a $Ca^{2+}$ ion, a $Na^+Cl$ ion pair and a number of stably bound water molecules. The inner most strands of each blade are all parallel and the $Ca^{2+}$ ion protrudes from the N-terminal end of the channel. The regions between the four blades are composed of hydrophobic residues (primarily Phe, Tyr and Trp) which are large enough to contact one another across such a wide interface. Connecting loops lay across the hydrophobic interface and connect adjacent blades. Blade IV is connected covalently to blade I via a disulfide bond between $Cys^{469}$ and $Cys^{660}$.

Identification of the TIMP-2 Binding Site in the GelA-CTD by Alanine Scanning Mutagenesis.

Figure 2:
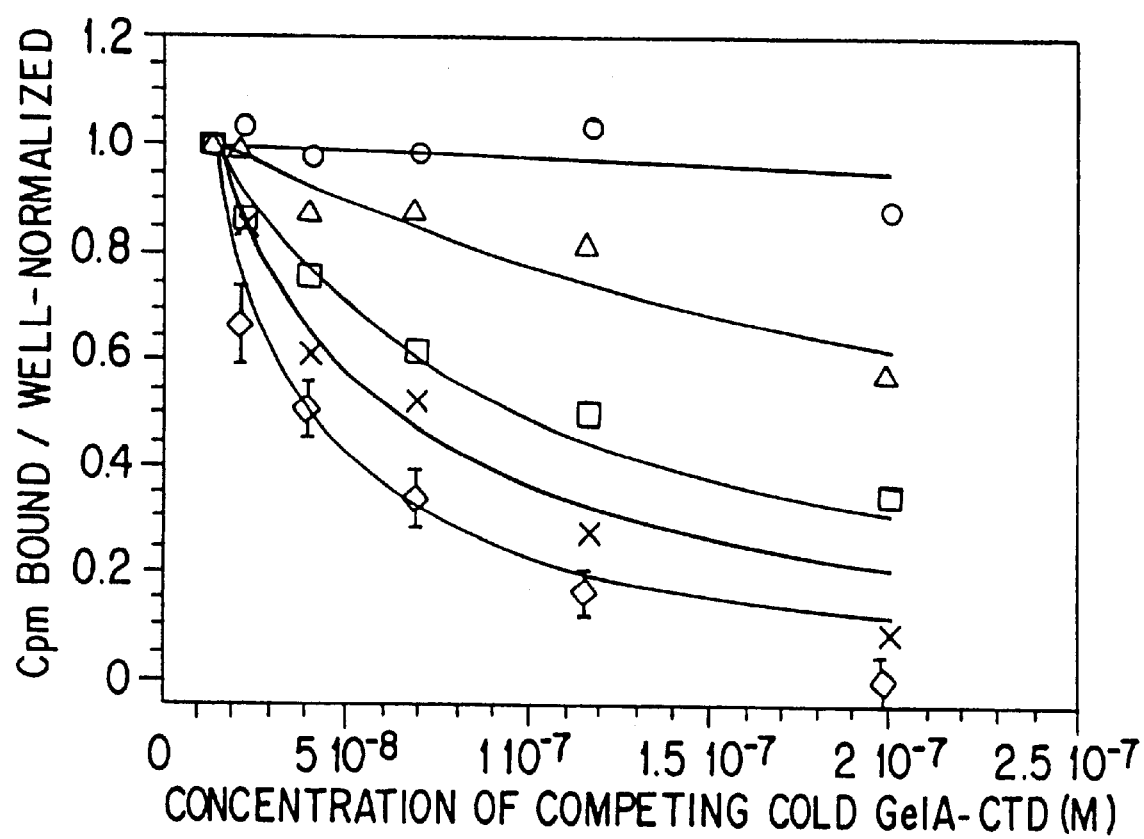

Alanine scanning mutagenesis of solvent exposed amino-acid residues of GelA-CTD) was used to define its molecular surface that interacts with TIMP-2. The results were interpreted by examination of the location and environment of each point mutant in the crystal structure of GelA-CTD (FIG. 1, 27), so that only residues of GelA-CTD which can directly interact with TIMP-2 are identified. Expression vector pFLAG72CT was mutagenized directly using PCR mediated site directed mutagenesis as described in Methods. All fifty resulting mutant proteins were purified as described previously (9,10) and assayed for TIMP-2 binding as described in Methods. The sequence of mutants that had negative effect on TIMP-2 binding was verified by sequencing of the entire coding region to exclude the appearance of secondary, PCR generated, mutations. To quantitate the TIMP-2 binding affinity of the different GelA-CTD mutants relative to wild type (WT) GelA-CIT we developed TIMP-2 binding and competition assay in 96 well modular plates. For binding experiments a solutions of $10^{-9}M$ of $^{125}I$-GelA-CTD containing increasing concentrations of competing cold ligand were added to TIMP-2 or BSA (control) coated wells and retained radioactivity was determined by counting individual wells as described in Methods. The apparent Ki for each mutant was determined by a fit of computer generated series of curves to the data from the competition assay. A 25% variation in apparent Ki thus determined produced curves which were clearly less representative of the data. An example of the results of this analysis for WT GelA-CTD and four mutants are shown in FIG. 2. The mutants presented in FIG. 2 were chosen to illustrate the range of variation encountered. All the mutants that had an effect on TIMP-2 binding (Ki/Kd>1) are summarized in Table 1. Substitution of Ala for one of the following amino acid residues $Lys^{470}$, $Arg^{482}$, $Arg^{491}$, $Arg^{495}$, $Asp^{501}$, $Glu^{515}$, $GlU^{518}$, $Lys^{519}$, $Glu^{529}$, $Lys^{531}$, $Glu^{539}$, $Glu^{549}$, Arg 550, $Asp^{564}$, $Arg^{567}$, $Lys^{578}$, $Asp^{586}$, $Lys^{596}$, $Asp^{608}$, $Asp^{618}$, $Hys^{628}$, $Lys^{633}$, $Lys^{639}$, $Glu^{641}$, $Lys^{649}$, $Leu^{638}$, $Gln^{643}$, and $Leu^{548}$ did not affect the binding affinity of GelA-CTD to TIMP-2 (Kd=Ki) in this assay. Single replacement of $Lys^{519}$ with Arg, $Ala^{479}$ with Thr, or $Leu^{548}$ with Arg also had no effect.

Localization of TIMP-2 Binding Residues on GelA-CTD.

Among all the point mutants of GelA-CTD which show a loss in binding, only $Asp^{569}$ is not considered part of the TIMP-2 binding surface. The remaining mutants all lie within two adjacent areas of the GelA-CTD shown as TIMP-2 Binding Surface-1 (TBS-1) and TIMP-2 Binding Surface-2 (TBS-2) in FIG. 1. The TIMP-2 binding site of GelA-CTD is divided into two regions in order to facilitate discussion of the different features seen in this broad binding site and to simplify comparison of these regions on related proteins. There is no physical basis for dividing the binding site into two regions, but we do so in order to discuss different features seen in the TIMP-2 binding site. TBS-1 is formed between blades III and IV and includes a non-polar interface composed of large aromatic residues (contacting $Trp^{574}$) which pack between the two adjacent blades and form a small, hydrophobic cavity. Surrounding this non-polar part of TBS-1 are a number of positively charged residues which are contributed mostly from the second ($Lys^{576}$, $Lys^{579}$), third ($Arg^{590}$), and fourth ($Lys^{604}$) strands of blade III as well as $Lys^{646}$ which is on a large turn made between the third and fourth strands of blade IV. The non-polar cavity is bounded by a looping strand which lies across the cavity and connects blades III and IV. This loop region, which contains $Asn^{611}$, is considered part of TBS-1 but is adjacent to TBS-2 and forms part of the putative TIMP-2 binding surface of GelA-CTD. TBS-2 contains residues required for TIMP-2 binding that are mostly located on blade IV. $PhC^{650}$ and $Gly^{651}$ are located on the fourth strand of blade IV. $Tyr^{636}$ comes from the third strand of blade IV but forms an adjacent surface with $Phe^{650}$ and $Gly^{651}$. $Asp^{656}$ is located on a single α-helical turn at the end of blade IV. $Asp^{615}$ is part of the loop section connecting blades III and IV, but is positioned adjacent to $Tyr^{636}$. Together, TBS-1 and TBS-2 make up the entire putative TIMP-2 binding surface of GelA-CTD. From FIG. 1, it can be seen that residues whose mutation caused at least 100-fold loss in TIMP-2 binding are predominantly found in TBS-1 in and about the cavity. $Asp^{615}$ is the only residue from TBS-2 which showed more 100 fold loss in TIMP-2 binding when mutated to alanine.

In modeling a TIMP-2 binding surface of GelA-CTD, it is possible to also make use of point mutations which had no effect on TIMP-2 binding. Some residues on GelA-CTD near or adjacent to the putative binding region did not impact TIMP-2 binding when mutated to alanine.

These mutants are considered boundary residues because they help define the outer limits of the TIMP-2 binding surface. They include $Lys^{578}$, $Asp^{586}$, $Asp^{608}$, $Asp^{618}$, $Lys^{633}$, $Lys^{639}$, $Glu^{641}$, $Gin^{643}$, and $Lys^{649}$. While the list is not an exhaustive one and does not completely surround the site, it is a considerable number, and as seen in FIG. 1, they contribute greatly to determining the shape of the TIMP-2 binding surface on GelA-CTD.

The effects of point mutations on GelA-CTD) binding of TIMP-2 can be characterized as 'direct' or 'indirect'. Point mutations with direct effect presumably show a loss in binding due to direct interaction with TIMP-2 since in the crystal structure these residues are almost entirely solvent exposed making no significant van der Waals contact, salt bridges or hydrogen bonds with nearby sidechain or backbone atoms. Those classed as 'indirect' are point mutants of residues which are involved in such interactions with neighboring atoms. The effect of these mutants on TIMP-2 binding may be either a result of loss of direct interaction with TIMP-2 or due to a perturbation of the local structure as a result of the point mutation which 'indirectly' causes a loss in TIMP-2 binding. Most of the point mutants which have an effect on TIMP-2 binding are classed as 'direct' including mutants of $Lys^{576}$, $Lys^{579}$, $Arg^{590}$, $Lys^{604}$, $Asn^{611}$, $Asp^{615}$, $Lys^{646}$, and $Phe^{650}$ (see Table 1). $Tyr^{636}$ may also be considered direct in that most of the ring including the hydroxyl group is solvent exposed and the van der Waals interactions of its $C_{\delta}1$ and $C_{\epsilon}1$ atoms are not likely to significantly perturb local geometry. The residues classed as 'indirect' are Asp569, $Trp5^{74}$, $Gly^{651}$, and $Asp^{656}$. The residues classed as 'indirect' are $ASp^{569}$, $Trp^{574}$, $Gly^{651}$, and $Asp^{656}$.

The entire TIMP-2 binding site shown in FIG. 3 represents a surface area of 1027 $Å^2$. The interior of the surface is defined by residues whose point mutants show a loss in TIMP-2 binding. The boundary of the surface is defined by the outermost residues which show an effect on TIMP-2 binding and by the boundary residues described above. In order to create the entire surface other residues for which mutations were not made needed to be included as part of the binding surface. These residues were selected by the criteria that they could have no atoms outside the boundary of the binding surface and must have surface accessible atoms within the interior of the surface. The non-mutated residues included as part of the TIMP-2 binding surface are residues $Asn^{577}$, $Tyr^{581}$, $Phe^{588}$, $Ala^{609}$, $Trp^{610}$, $Ala^{612}$, $Ilc^{613}$, $Pro^{614}$, $Leu^{645}$, and $Val^{648}$ as well as the $C_{\zeta}$ and $C_{\epsilon}1$ ring carbons of $Phe^{602}$. All the aromatic residues of this group as well as $Leu^{645}$ contribute to form the non-polar cavity in TBS-1. $Ala^{612}$, $IlC^{613}$, and $Pro^{614}$ are on the loop connecting blades III and IV. $Ilc^{613}$ is unique in that only its backbone atoms are surface accessible. $Val^{648}$ makes up part of the van der Waal contact surface of TBS-2. The hole in the binding surface is present because $Leu^{638}$ (which is in a small depression between $Phe^{650}$ and $Tyr^{636}$) did not show a loss in TIMP-2 binding when mutated to alanine. Thus, the $C_{\gamma}$, $C_{\delta}1$ and $C_{\delta}2$ atoms of $Leu^{638}$ are not considered part of the TIMP-2 binding surface. Rationalizing the effects of these mutations on TIMP-2 binding requires a broader description of the structural environment of these residues.

Structural Analysis of 'Indirect' Mutants

As discussed above, a some of the residues included in the TIMP-2 binding site of GelA-CTD may be classed as 'indirect' mutants including $Asp^{569}$, $Trp^{574}$, $Gly^{651}$, and $Asp^{656}$. Here, we rationalize the effects of mutating them to alanine on TIMP-2 binding given the fact that these residues also interact with other portions of the GelA-CIT) molecule. The $O_{\delta 1\ of\ Asp}{}^{569}$ forms a hydrogen bond with a backbone amide proton of $Gly^{585}$ which is located on a tight turn formed between the second and third strands of blade III. The $Asp^{569}$->Ala mutation causes only a small reduction in TIMP-2 binding. Strand three of blade III contains a residue, $Arg^{590}$, whose mutation to alanine shows a large loss in binding (>100-fold) and directly interacts with TIMP-2. Also, Asp569 is away from the contiguous binding surface formed by the other point mutants which affect TIMP-2 binding. While it is possible that TIMP-2 directly interacts with $Asp^{569}$, the effect of the $Asp^{569}$->Ala mutation is most likely mediated by alteration of the position of $Arg^{590}$ as a result of the loss of an important structural H-bond with $Gly^{585}$ which constrains the conformation of the turn.

$Trp^{574}$ is one of a number of hydrophobic residues forming the pocket between blades III and IV. It makes van der Waals contact with a number of atoms from neighboring sidechains including $Tyr^{581}$ and $Trp^{610}$. Since only the $C_{\zeta}3$ and $C_{\eta}2$ atoms of $Trp^{574}$ are surface accessible, the large loss in binding of the $Trp^{574}$->Ala mutant is most likely not due to a loss in the interaction of these atoms with TIMP-2 but to a rearrangement of neighboring residues as a result of the mutation. The most reasonable interpretation of the effect of the mutation is that TIMP-2 makes van der Waals contact with this pocket upon binding GelA-CTD and that $Trp^{574}$->Ala disrupts TIMP-2 binding by altering the van der Waal surface presented by GelA-CTD. So while the effect of the $Trp^{574}$->Ala mutation is 'indirect', it is suggestive of direct binding of TIMP-2 to surface atoms in the pocket.

The $Gly^{651}$->Ala mutation has a moderate effect on TIMP-2 binding. Since alanine, by virtue of its $C_{\alpha}$, is sterically restricted in its allowable $\phi$, $\psi$ angles, it is possible that the effect on TIMP-2 binding of the $Gly^{651}$->Ala mutation is the result of alteration in the protein backbone. Alanine is more energetically restricted than glycine in the $\phi$, $\psi$ conformations it may adopt. However, since $Gly^{651}$ is found in a well formed β-sheet of the outer most β-strand of blade IV and adopts phi psi angles ($\phi$=−157.9, $\psi$=−174.8) commensurate with an anti-parallel β-stand conformation, alanine is likely to adopt the same conformation at the site. Thus, loss in TIMP-2 binding for the alanine mutant is due to the addition of the $C_{\beta}$ atom on residue 651 which, by approximation, blocks interaction of TIMP-2 with the $C_{\alpha}$ of 651. The double mutant, $Glu^{654}$->Ala/$Gly^{651}$->Arg shows>100-fold loss in TIMP-2 binding. $Glu^{641}$ is entirely solvent exposed and does not interact with neighboring atoms, and the single mutant, $Glu^{641}$->Ala shows no effect on TIMP-2 binding. Since $Glu^{641}$ is entirely solvent exposed does not appear to interact with any neighboring atoms, the effects of the double mutant are not considered to be a result of cooperativity. Thus, the effect of the double mutant is due exclusively to the $Gly^{651}$->Arg mutation. Presumably, the $Gly^{651}$->Arg mutant covers a nearby surface on GelA-CTD upon which TIMP-2 normally binds. Since arginine is much larger than alanine and is also charged, it is not surprising that it had a much more dramatic effect on TIMP-2 binding than alanine. The fact that both $Gly^{651}$->Ala and $Gly^{651}$->Arg reduce TIMP-2 binding suggests that TIMP-2 contacts GelA-CTD at the $C_{\alpha}$ of $Gly^{651}$ as well as surface residues near $Gly^{651}$. $Asp^{656}$ is solvent exposed and forms an H-bond with the hydroxyl group of $Tyr^{637}$. The effect on TIMP-2 binding of the $Asp^{656}$->Ala mutation may be a result of perturbation of the orientation of $Tyr^{637}$ by loss of this H-bond. While it is possible that TIMP-2 interacts with only Tyr$^{637}$, the simplest interpretation of the effect of the mutation is that Asp$^{656}$ directly interacts with TIMP-2. This conclusion would partially explain the large loss in TIMP-2 binding of the Gly$^{651}$->Arg mutation which puts a positive charge near Asp$^{656}$. Also, Asp$^{656}$ forms a contiguous surface with Gly$^{651}$, Phe$^{650}$, and Tyr$^{636}$ (other TIMP-2 binding residues). TIMP-2 may interact with Tyr$^{637}$ but that residue was not mutated in the study so it cannot explicitly be considered as part of the TIMP-2 binding surface of GelA-CTD.

Comparison of GelA-CTD and Interstitial Collagenase.

Figure 4A:
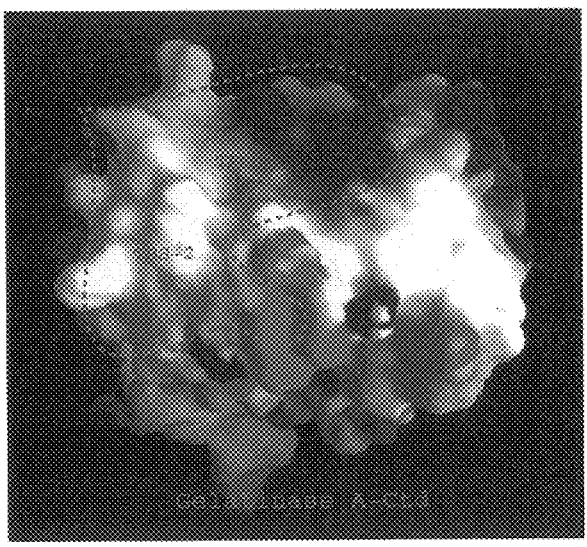
Figure 4B:
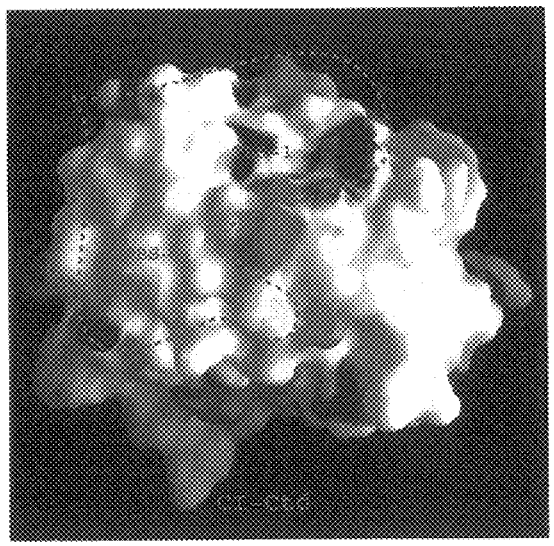

Having defined a TIMP-2 binding site on the surface of GelA-CTD, it is instructive to compare the known structure of the C-terminal domain of interstitial collagenase (ClI-Ctd) (29) which does not bind TIMP-2 to identify which structural features of the TIMP-2 binding site are shared and which are divergent. It was surprising to find that many of the positively charged residues are conserved both in terms of sequence and structure. Lys$^{579}$, Arg$^{590}$, and Lys$^{604}$ of GelA-CTD are conserved in ClI-Ctd and adopt similar conformations in the structures (FIGS. 3 and 4). Furthermore, Lys$^{646}$ in GelA-CTD aligns with Arg$^{453}$ in ClI-Ctd, so while the sequence is not identical, charge is conserved and the residues overlay well when their C$_\alpha$ atoms are aligned. Point mutants of Arg$^{590}$ and Lys$^{646}$ all show at least 100-fold loss in TIMP-2 binding in GelA-CTD. Lys$^{576}$, which also shows over a 100-fold loss in TIMP-2 binding when mutated to alanine, is not conserved in ClI-Ctd where it becomes a negatively charged Asp residue. It is interesting to note that some of the charged residues, like Arg590 and Lys646, which seem to make a large contribution to TIMP-2 binding are also conserved in a ClI-Ctd which does not bind TIMP-2. Clearly, other features of GelA-Ctd, which are not found in ClI-Ctd, must be identified to account for its TIMP-2 binding properties.

Further examination of the aligned structures reveals that the non-polar cavity in GelA-CTD is covered by a number of negatively charged residues in ClI-Ctd. Trp$^{574}$, Lys$^{576}$, and Ala$^{609}$ of GelA-CTD align with negatively charged residues of ClI-Ctd. In ClI-Ctd, Asp$^{385}$ is on the periphery of the pocket; Glu$^{383}$ protrudes from the pocket and Glu$^{418}$ extends over the pocket. The effect of these negative charges on TIMP-2 binding is still not known but their negative potential could shield the nearby positive charges from TIMP-2. Alternatively, if TIMP-2 does make van der Waals contacts with the non-polar cavity of GelA-CTD, the effect of all the charged groups in the cavity would be to block this interaction and in fact bury the negative charges inside the TIMP-2/GelA-CTD binding interface. The negative potential in the cavity of ClI-Ctd is partially reduced by the presence of Lys$^{452}$ which is Leu$^{645}$ in GelA-CTD. Leu$^{645}$ is a non-polar residue which points into the hydrophobic cavity of TBS-1. FIG. 3 shows the charge potentials of both GelA-CTD and ClI-Ctd as calculated and displayed by GRASP. Comparison of the TBS-1 regions of GelA-CTD) and ClI-Ctd suggests qualitatively that the pockets formed present different accessible surfaces. Some residues in the pocket are conserved, notable exceptions are Trp$^{610}$ and Phe$^{588}$ of GelA-CTD). Other differences are seen in the loop connecting blades III and IV. Here, ASp$^{615}$ becomes isosteric, but uncharged Asn$^{424}$ in ClI-Ctd, while Asn$^{611}$, Ala$^{612}$, Pro$^{614}$ of GelA-CTD are changed to other residues in ClI-Ctd. Only Ile$^{623}$ is conserved but this residue has only backbone atoms which are surface accessible in the structure. Clearly, GelA-CTD and ClI-Ctd would present a very different charge distribution and contact surface along their connecting loops.

Comparison of TBS-2 of the aligned molecules, reveals more subtle effects. Phe$^{650}$, which protrudes out into solvent in the GelA-CTD, as well as Tyr$^{636}$, Gly$^{65}$1 and Asp$^{656}$ are not conserved in ClI-Ctd. Again, these changes create both a different contact surface and different surface potentials which would reduce the possibility of ClI-Ctd binding TIMP-2 at this region.

Comparison of Related Sequences

A sequence alignment of other MMP C-terminal domains was performed (FIG. 5) to see if features noted in the comparison of ClI-Ctd and GelA-CTD held true for other MMP family members particularly those not known to bind TIMP-2. One of the most striking features of the alignment is how well conserved some of the residues necessary for full TIMP-2 binding are throughout many members of the MMP family. Just as in the comparison with ClI-Ctd, Lys$^{579}$, Arg$^{590}$, Lys$^{604}$ and Lys$^{645}$ are well conserved in many members of the family. GelB-CTD shows the least homology among this group of positively charged residues. Also, the negative charges in ClI-Ctd, which occurred at Trp$^{574}$, Lys$^{576}$, and Ala$^{609}$ in GelA-CTD are also seen in many of the members of the MMP family. Only GelA, GelB and MT1-MMP do not place negative charges in the cavity. Further examination of the sequence alignment shows that GelA-CTD has very little homology with other member in the region between Ala$^{609}$–Pro$^{614}$. These residues make up the loop region which connect blades III and IV. Other members show a lot of homology over the region and fit well to a DFPGIX (where X is either G, D, E or P) consensus sequence. It is interesting to note that GelA is only homologous in this region at Ile$^{613}$ whose sidechains is buried in the structure and could not interact directly with bound TIMP-2.

The alignment of residues from the TBS-2 region shows that GelA and GelB are most similar, although not identical, over this stretch. Many of these residues, except for Leu$^{645}$ and Lys$^{646}$, make up most of what is considered TBS-2 in GelA-CTD. Asp$^{615}$ is also considered part of TBS-2 and is homologous in GelB. MT1-MMP and stromelysin-3 are the next most similar with residues which are identical to or make conservative substitutions at Asp$^{615}$ and Asp$^{656}$.

Comparison of GelA-CTD and GelB-CTD

A comparison of aligned structures made between GelA-CTD and the model of GClB-CTD shows they share more homology over the TIMP-2 binding surface than ClI-Ctd. As seen from the sequence alignment, residues in TBS-2 were highly homologous. Tyr$^{636}$, Val$^{648}$, Gly$^{651}$, Asp$^{615}$ and Asp$^{656}$ from GelA-CTD are structurally conserved in GelB-CTD. Only one residue is significantly different, Phe$^{650}$ becomes Val$^{694}$ in GelB-CTD. The turn connecting the third and fourth strands of blade IV required rebuilding in GelB-CTD due to the insertion of residues. But for the most part, these residues were arranged similarly in both structures. The loop connecting the third and fourth strand of blade IV had to be rebuilt to accommodate the insertion of two residues. This increased the size of the loop, but still placed Leu$^{688}$ and Asn$^{689}$ of GelB-CTD near Leu$^{645}$ and Lys$^{646}$ of GelA-CTD. So while no new charges are introduced, the contact surface in this region would be somewhat different in GelB-CTD.

In contrast to TBS-2, TBS-1 of the model of GelB-CTD diverges dramatically from GelA-CTD. A great number of changes have been made in the non-polar cavity residues. Trp$^{574}$, Tyr$^{581}$, Phe$^{588}$, Phe$^{602}$, and Trp$^{610}$ are not conserved in GelB-CTD. The sequence changes make the cavity much deeper in GelB-CTD with a cavity floor defined by the contribution of non-polar atoms from Leu688 and Met$^{653}$. Other residues conserved between the two in TBS-1 are some of the positively charged residues which lie about the cavity. $Lys^{579}$ and $Arg^{590}$ of GelA-CTD are conserved in GelB-CTD. GelB-CTD makes a conservative substitution at $Lys^{576}$ where the positive charge is conserved. Other positive charges, such as $Lys^{604}$ and $Lys^{646}$ of GelA-CTD, become polar, but uncharged residues in GelB-CTD. Overall, there are fewer positively charged residues in the TBS-1 region of GelB-CTD than found in either GelA-Ctd or ClI-Ctd. The loop region connecting blades III and IV in GelB-CTD, which shows intermediate homology to GleA-CTD, required slight rebuilding due to the insertion of $Leu^{659}$ in GelB-CTD. The insertion makes it impossible to model the $C_\alpha$ positions of the loop residues identically, so it is modeled to have a different structure than either GelA-CTD of ClI-Ctd. $Pro^{614}$ of GelA-CTD is conserved in GelB-CTD but does superimpose due to the rebuilding of the loop. $Asn^{611}$ and $Ala^{612}$ are different in GelB-CTD, but are identical to residues seen in the ClI-Ctd structure.

Mutants of GelA-CTD That Don't Inhibit Membrane Dependant Activation of GelA Are Clustered Within The TIMP-2 Binding Site.

Interaction of the GelA-CTD with cell surface is essential for activation of the pro-enzyme. Consequently membrane dependent activation of GelA is competitively inhibited in the presence of the recombinant GelA-CTD (see introduction and discussion). The results we have reported earlier support the hypothesis that assembly of MMP/TIMP-2/GelA-CTD complex promotes activation of GelA and inhibition of GelA activation in the presence of excess of GelA-CTD is due to a direct competition with the binding of GelA to the inhibitor TIMP-2 in the complex. A direct approach to the question whether the assembly of this complex is indeed a prerequisite for GelA activation is to determine whether activation inhibition and TIMP-2 binding properties of GelA-CTD can be separated. Therefore we investigated the ability of all 50 GelA-CTD mutants described above to inhibit membrane dependent activation of GelA in vitro. Increasing amounts of purified WT or mutant GelA-CTD protein was added to membrane GelA activation reaction and the amount of remaining proenzyme species, a measure of activation inhibition, was analyzed on zymograms. The results are presented in FIG. 6. Most noticeable, is the fact that point mutations outside of the TIMP-2 binding site have inhibited GelA activation as did WT GelA-CTD ($T2+Ai^+$ phenotype). Furthermore, the only point mutations which showed a loss in activation inhibition were those found in the TIMP-2 binding site described above. However, mutants that exhibited a dramatic loss of TIMP-2 binding activity (Ki/Kd>100) segregated into two groups. Mutants of $Lys^{576}$, $Arg^{590}$, and $Trp^{574}$ completely failed to inhibit GelA activation ($T2^-Ai^-$ phenotype). Mutants of $Asp^{615}$, and $Lys^{646}$ were indistinguishable from WT, while mutant $Glu^{641}+Gly^{651}\rightarrow Arg$ shown only a slight loss of activation inhibition activity. Mutants $Asp^{656}$ and $Tyr^{636}$ exhibited a significant loss of TIMP-2 binding (Ki/Kd=10) and a comparable loss of activation inhibition activity. Mutant $Lys^{604}$ showed a considerable loss in TIMP-2 binding (Ki/Kd=25) but had little or no effect on activation inhibition. All other mutants (see table 1 and FIG. 6) characterized by a very moderate loss of TIMP-2 binding (Ki/Kd<10) and were indistinguishable from WT in the activation inhibition assay. Thus point mutants of residues in the TIMP-2 binding site do not always show a complete correlation between the degree of loss of TIM P-2 binding and their respective loss of activation inhibition activity. Mutants that do show such correlation are distributed between TBS1 and 2. Those with severe loss of both functions ($Trp^{574}$, $Lys^{576}$, and Arg590) are clustered together in the TBS-1 region of the TIMP-2 binding site (see FIG. 1). Two mutants with moderate effect on both functions ($Asp^{656}$ and $Tyr^{636}$) are found in TBS2. Two mutants with the greatest disparity in effect on TIMP-2 binding and activation inhibition ($Asp^{615}$ and $Lys^{646}$) are found on the border between TBS1 and 2. Finally it is important to note an absence of the mutants with $T2b^+Ai^-$ phenotype.

Discussion.

Since GelA-CITD displays pseudo four-fold symmetry, it is interesting to consider what structural features distinguish the TIMP-2 binding site located roughly at the interface between blades III and IV from similar sites which would be found at the interfaces between the three other blades. A GRASP representation of the GelA-CTD structure with electrostatic potentials displayed at the surface of the molecule shows that the interface between blades III and IV is unique in having a high concentration of positive charge (FIG. 3) located near the interface. Furthermore, the outermost strand of blade IV is unique in the GelA-CTD structure in that it forms a regular anti-parallel β-strand with no β-bulges as seen in blades II and III. The fourth strand of blade 1 contains no β-bulges, but its backbone H-bonding pattern with the third strand is significantly distorted by the presence of cis proline, $Pro^{506}$. Cis prolines are identified in the fourth strands of all the blades except IV. Thus, the highly localized positive charge and a canonical β-strand conformation of an adjacent blade would, in part, create a unique binding surface which would not be found at related positions of this highly symmetrical molecule.

Having defined a TIMP-2 binding site on GelA-CTD, it is possible to look at known structures and sequences of related MMPs and develop an idea of how binding and specificity are achieved. The two basic assumptions in such an analysis are that 1) all related MMP sequences adopt the same fold as described for GelA-CTD and ClI-Ctd and 2) TIMP-1 binds Gel B-Ctd in a manner comparable to the TIMP-2 binding of GelA-CTD. If these two assumptions are true than some interesting observations on the nature of TIMPs binding to MMPs may be credibly made and are discussed below.

1) The positively, charged residues in TBS-1 of GelA-CTD are required but not sufficient for binding TIMP-2.

While the mutation studies show that these residues are clearly required for full TIMP-2 binding activity, the fact that many of these charged residues are conserved in MMPs which are not known to bind TIMP-2 suggests that the presence of these residues is not sufficient for causing TIMP-2 binding. TIMP-2 has a negatively charged C-terminal tail sequence, EFLDIEDP, which when removed shows a reduced binding kinetics profile similar to that of TIMP-1 (30). TIMP-1 does not have a negatively charged sequence at its C-terminus. Since electrostatic forces often effect long range interactions between molecules, the positive charges may serve to draw the TIMP-2 molecule near the binding site of GelA-CTD prior to docking. Once bound, the electrostatic interactions are maintained, but van der Waal forces predominate in directing full, specific binding. It is possible that the negative charges described in the TBS-1 region of other non-TIMP binding MMPs reduce the effect of the long range interaction and also minimize the electrostatic interaction between the negatively charged TIMP-2 sequence and the conserved positively charged residues of these MMPs. It is also interesting to note that Gel B, which specifically binds TIMP-1, has two fewer positively charged residues than GelA in the TIMP-2 binding surface. Perhaps, these two residues, $Lys^{604}$ and $Lys^{646}$, play a role in binding the negatively charge tail of TIMP-2. Also, Lys$^{595}$ and Lys$^{597}$, which were not mutated in this study, but are near the binding site, may interact with the TIMP-2 tail. Lys$^{597}$ is of particular interest since it is not conserved in any of the other MMPs.

2) Interaction With TBS-1 Is Likely To Contribute More Than TBS-2 to Specificity of TIMP-2 Binding to GelA-CTD.

GelA-CTD and Gel B-CTD share considerable homology in the TBS-2 region so specificity will most likely not be determined in that region. Presumably, TIMP-1 and TIMP-2 will bind the TBS-2 region similarly in both molecules. The region of the TIMP-2 binding site that diverges the most between GelA and B are found in TBS-1. Here, Gel B is missing two positively charged residues. Also, sequence analysis and model comparison show the two would have different non-polar cavities. The Gel B cavity is deeper and broader than that of GelA. Furthermore, the loop Ala$^{609}$–Asp$^{615}$ connecting blades III and IV of GelA-CTD is different than that of Gel B-Ctd. The loop differs in both sequence and backbone structure by virtue of an insertion of a Leu residue in the Gel B sequence.

3) Van der Waal forces play a major role in TIMP-2 binding and specificity.

The TIMP-2 binding site of GelA-CTD represents a broad surface which is conservatively estimated to cover just over 1000 Å$^2$ and is composed mainly of uncharged residues. Of the charged residues in the binding site, many are found in the C-terminal domains of non-TIMP binding MMPs suggesting that the presence of the charged residues alone is not enough to account for binding. Likewise, the fact that GelA-CTD shares so many charged residues in common with Gel B-Ctd suggests that specific binding of TIMP-2 is not a result of simple electrostatic interactions. Most likely, the strength and specificity of the binding comes as much from van der Waal interactions as from electrostatic attraction. Biochemical studies have shown that TIMP-2 binding to GelA-CTD is sensitive to low pH and ionic detergent but resistant to high salt (20,30). These results suggest that there is both a significant ionic and van der Waal component to the TIMP-2 binding of GelA-CTD. The TIMP-2 binding site of GelA-CTD described in this paper represents a broad surface of approximately 1000 Å$^2$ with a high positively charged region clustered about a hydrophobic cavity and an extended, mostly uncharged, van der Waal contact surface. The charged region of the site accounts for the pH and ionic strength dependence of binding, while the cavity and broad, van der Waal surface of the site accounts for the requirement of detergent to fully disassociate the complex.

One of the most prominent sequence characteristics of non-TIMP binding MMPs is their propensity to have negatively charged residues in or near the cavity in TBS-1. These charges were seen as potentially having a detrimental effect on TIMP-2 binding. As noted earlier, besides GelA and B, only MT1-MMP is identified as not having negative charges at residues found in or near the cavity. Furthermore, as seen in FIG. 4, many of the sequence features shared by GelA and B are also found in MT1-MMP. Pro$^{614}$, Asp$^{615}$, and Asp$^{656}$ residues of GelA are conserved in MT1-MMP as well. While there are still many sequence features among the TIMP-2 binding site residues not shared by GelA and MT1-MMP, MT1-MMP is by far the most homologous of the non-Gelatinase MMPs. Taken together, these observations suggest that MT1-MMP may be able to bind TIMP-2. In fact recent observations support this conclusion (25,26).

Interaction of inhibitors with pro-gelatinases is mediated by its C-terminal domain (20–22). The TIMP-2 C-terminal domain is 67 residues long from Cys$^{128}$–Pro$^{194}$. It has six cysteines which, by analogy to TIMP-1, are assumed to form three disulfide bonds (31). Thus, the C-terminal domain of TIMP-2 is likely to be compact and globular. The C-terminal portion is separated from the N-terminal-domain by only a single residue, Glu$^{127}$, so the N- and C-terminal domains of TIMP-2 must be located extremely close to one another in space. Given the large surface area of the TIMP-2 binding site of GelA-CTD, it is possible that portions of the N-terminal domain of TIMP-2 also participate in binding. Since the N-terminal domains of TIMP-1 and TIMP-2 show greater homology (44% identity) than their respective C-terminal domains (27% identity) and the TBS-2 sections of GelA and B are far more similar than their TBS-1 regions, it is possible that portions of the N-terminal domain of TIMP-2 binds blade IV residues of Gel-Ctd. This would mean that TBS-1 of GelA-CTD is bound by the C-terminal portion of TIMP-2. As stated above, the C-terminal domain of TIMP-2 contains a negatively charged sequence which is required for full binding activity. TBS-1 has a lot of positively charged residues, particularly in GelA, and based on sequence and model comparison of GelA and B shows far less sequence and structural homology than in TBS-2. For this reason, it is likely that TBS-1 of GelA determines its specificity for TIMP-2 as opposed to TIMP-1. Furthermore, assuming the C-terminal domain of TIMP-2 is not elongated, portions of TBS-2 may in fact bind parts of the N-terminal domain of TIMP-2.

GelA is a multi-domain protein containing a catalytic domain, a domain with thrice type II fibronectin-like repeats, and a C-terminal domain. The quaternary arrangement of these domains is still unknown. Biochemical evidence from deletion studies and crosslinking experiments suggest that active GelA is bound simultaneously at its catalytic and C-terminal domains by the N-terminal and C-terminal domains of TIMP-2. TIMP-2 is a relatively small, globular protein (MW=21 kDa) whose N-terminal portion is compact, adopts an OB-fold (32), and competitively inhibits substrate cleavage by binding the catalytic domain of MMPs. Given the TIMP-2 binding site described in the paper, it may be assumed that the active site of the catalytic domain is located relatively near the interface between blades III and IV of the C-terminal domain when bound to TIMP-2. Whether the domains of GelA adopt a rigid conformation or tumble freely in solution has yet to be determined and is the subject of future study.

Mechanism of Cell surface GelA Activation.

The soluble MMP, GelA, is recruited to the cell surface where it is activated in a MT1-MMP dependent fashion (reviewed 33). The initial MT1-MMP dependent Asn$^{37}$-Leu pro-peptide cleavage is inhibited by excess of TIMP-2 and competitively inhibited by GelA-CTD. Accordingly, truncated GelA that lacks its C-terminal domain is not activatable by this mechanism (13). Thus compelling evidence supports the role of GelA-CTD in recruitment of the proenzyme to the cell surface that is a prerequisite to its activation. The role of TIMP-2 in this mechanism is more controversial. It is clear that the recombinant GelA-CTD can interact with cell surface via binding to the activated MT1-MMP/TIMP-2 complex to form a tri-molecular complex of activated MT1-MMP/TIMP-2/GelA-CTD. It is also possible to demonstrate that carefully titrated amounts of TIMP-2 can increase the efficiency of activation in cell membrane dependent, TIMP-2 depleted system. These results support the hypothesis that assembly of MT1-MMP/TIMP-2/GelA-CTD complex promotes cell surface GelA activation. Conversely, it has become evident that soluble MT1-MMP lacking its transmembrane domain can faithfully cleave GelA propeptide at $Asn^{37}$-Leu (26). In this soluble purified system, TIMP-2 functions solely as a specific MT1-MMP inhibitor. Cleavage of the GelA propeptide does not depend on the presence of its C-terminal domain and, contrary to membrane dependent GelA activation, truncated GelA is a substrate for soluble activated MT1-MMP. Thus it is essential to ascertain by other approaches whether the assembly of the MT1-MMP/TIMP-2/GelA complex on the cell membrane is indeed a prerequisite for GelA activation.

Since inhibition of GelA activation in the presence of excess of GelA-CTD is due to a direct competition with the cell surface binding of GelA, a powerful approach to the above question is to determine whether activation inhibition and TIMP-2 binding properties of GelA-CTD can be separated. Our previous experiments using chemical and protcolytic modifications of GelA-CTD failed to achieve such an effect (9,10). All manipulations of GelA-CTD abolished both its TIMP-2 binding and the inhibitory activity in the membrane activation assay. Mutagenesis provides an infinitely better approach to address this question. A complete correlation between loss of activation inhibition function and the ability to bind TIMP-2 can be a conclusive evidence that TIMP-2 serves as a mediator of GelA activation, provided that a sufficient number of the TIMP-2 binding site mutants were analyzed. Here, we investigate the ability of all fifty GelA-CTD mutants described above to inhibit membrane dependent activation of GelA in vitro. All mutants outside of the TIMP-2 binding site inhibit GelA activation as well as WT GelA-CTD (T2$^+$Ai$^+$ phenotype). Mutants that exhibited a dramatic loss of TIMP-2 binding activity (Ki/Kd>100) segregated into classes. Mutants with alanine substitution of Lys$^{576}$, Arg$^{590}$, and Trp$^{574}$ failed to inhibit GelA activation (T2b$^-$Ai$^-$ phenotype). Asp$^{615}$, and Lys$^{646}$ mutants were indistinguishable from WT, while a double with alanine substituting for Glu$^{641}$ and Arg for Gly$^{651}$ shown only a slight loss of activation inhibition activity. Other mutants in the TIMP-2 binding site show moderate to no effect on activation inhibition.

Importantly no mutants with T2$^+$Ai$^-$ phenotype were found. Thus, although all Ai$^-$ mutants are concentrated in the TIMP-2 binding site, and no T2b$^+$Ai$^-$ mutants were isolated, the correlation between loss of TIMP-2 binding and activation inhibition properties of GelA-CTD mutants is not absolute. This inconsistency can be explained by differences in the assays used to measure the effects of the point mutations. For example, only a part of the TIMP-2 binding site of GelA-CTD described here actually interacts with TIMP-2 bound to MT1-MMP. This may be due to the nature of TIMP-2 interaction with MT1-MMP that exposes only a portion of TIMP-2 C-terminal domain necessary to engage the entire GelA-CTD binding site. Thus only a fraction of mutants in the GelA-CTD TIMP-2 binding site loses the capacity to competitively inhibit activation (T2$^-$Ai$^-$). In this case the assembly of MTl-MMP/TIMP-2/GelA complex is still a prerequisite for GelA activation and the question remains how the MT1-MMP occupied and inhibited by TIMP-2 is able to cleave the GelA propeptide. Several explanations can be invoked for the mechanism of this reaction. An activation model can be proposed where MT1-MMP/TIMP-2 complex acts as a receptor for soluble GelA and forms a tri-molecular presentation complex. Another molecule of TIMP-2 free MT1-MMP may then perform the Asn$^{37}$-Leu pro-peptide cleavage. As a result, activation of GelA is sensitive to the ratio of the unoccupied activated MT1-MMP to MT1-MMP/TIMP-2 complex and saturating amounts of TIMP-2 inhibit activation.

A second set of GelA activation models can be proposed based on the data presented here, if the existence of T2$^-$Ai$^-$ and T2$^-$Ai$^+$ mutants is interpreted to mean that GelA-CTD binds to another, yet to be identified, cell surface receptor and the resulting complex is activated by TIMP-2 free MT1-MMP. For example, binding of the GelA-CTD can occur through interaction with $\alpha$ V$\beta$5 integrin as recently reported (34). The results of mutagenesis indicate that TIMP-2 and putative receptor binding sites on GelA-CTD overlap since no Ai$^-$ mutants were found outside of the TIMP-2 binding site. This overlap can potentially explain why TIMP-2 can inhibit binding of GelA to the cell surface even in the case that it is mediated by a receptor other than MT1-MMP/TIMP-2 complex. Earlier we have described an analogous but soluble complex of GelB/CII where the CII and TIMP-1 binding sites of GelB-CTD overlap (22).

TABLE 1

Gel A-CTD mutants that affect its TIMP-2 binding activity (Ki/Kd > 1). Wild type Kd and mutant Ki was determined as in FIG. 2. D and ID - mark mutants affecting TIMP-2 binding directly and indirectly respectively.

| Mutant # | Ki/Kd | Mutant # | Ki/Kd |
|---|---|---|---|
| #28 ID Asp$^{569}$→Ala | 8 | #247 D Lys$^{646}$→Ala | >500 |
| #31 D Lys$^{579}$→Ala | 6 | #250 D Trp$^{574}$→Ala | >500 |
| #39 D Lys$^{604}$→Ala | 25 | #252 D Tyr$^{636}$→Ala | 10 |
| #41 D Asp$^{615}$→Ala | 300 | #255 D Phc$^{650}$→Ala | 8 |
| #46 ID Glu$^{641}$ → Ala + Gly$^{651}$ → Arg | >500 | #257 D Gly$^{651}$→Ala | 3 |
| #229 D Lys$^{576}$→Ala | ≧500 | #258 ID Asp$^{656}$→Ala | 10 |
| #234 D Arg$^{590}$→Ala | >500 | #259 D Asn$^{611}$→Ala | 3 |

References

1. Birkedal-Hansen, H. (1995) Proteolytic remodeling of extracelular matrix. Curr. Opin. Cell Biol. 7:728–735.
2. Kleiner, D. E., and Stetler-Stevenson, W. G. (1993). Curr. Opin. Cell Biol. 5:891–897.
3. Matrisian L M. (1992 ) [Review] Bioessays. 14(7):455–63.
4. Stetler-Stevenson W G., Aznavoorian S., Liotta L. A. (1993) [Review] Annual Review of Cell Biology. 9:541–73.
5. Stetler-Stevenson W G., Liotta LA., Klciner D E Jr. (1993) [Review] FASEB Journal. 7(15):1434–41.
6. Liotta, L. A., Steeg, P. S., and Stetler-Stevenson, W G. (1991) Cell 64:327–336.
7. Khokha, R., Waterhouse, P., Yagel, S., Lala, P. K., Overlal, C. M., Norton, G., and Denhardt, D. T. (1989) Science 243:947–950.
8. Sato H. Takino T. Okada Y. Cao J. Shinagawa A. Yamamoto E. Seiki M. Nature. 370(6484):61–5,1994
9. Strongin A Y, Marner B L, Grant G A, Goldberg G I., (1993) J. Biol. Chem.; 268:14033–14039
10. Strongin, A. Y., Collier, I. E., Bannikov, G., Marmer, B. L., Grant, G. A., Goldberg, G. I. (1995) Journal of Biol. Chem. 270(10):5331–8.
11. Ward R V. Atkinson S J. Slocombe P M. Docherty A J. Reynolds J J. Murphy G. (1991) Biochimica et Biophysica Acta. 1079(2):242–6.
12. Azzam H S. Thompson E W. (1992) Cancer Research. 52(16):4540–4.

13. Murphy G. Willenbrock F. Ward R V. Cockett M I. Eaton D. Docherty A J. (1992) Biochemical Journal. 283 ( Pt 3):637–41.
14. Brown P D. Kleiner D E. Unsworth E J. Stetler-Stevenson W G. (1993 )Kidney International. 43(1):163–70.
15. Seltzer J. L., Lee A. Y., Akers K. T., Sudbeck B., Eileen A. Southon, Wayner E. A., Eisen A. Z. (1994) Experimental Cell Research 213(2):365–74.
16. Overall C M, Sodek J. (1990) 1. Biol. Chem 265, 21141–51
17. Collier, I. E., Wilhelm, S. M., Eisen, A. Z., Marmer, B. L., Grant, G. A., Seltzer, J. L., Kronberger, A. M., He, C., Bauer, E. A., and Goldbcrg, G. I. (1988) J Biol Chem 263(14):6579–6587.
18. Atkinson, S. J., et al.(1995) J. Biol. Chcm. 270:30479–30484.
19. Hiroshi Sato, Takahiso Takino, Takeshi Kinoshita, Kazushi Imai, Yasunori Okada, William G. Stetler-Stevenson, Motoharu Sciki. (1996) FEBS Letters 385, 238–240,.
20. Goldberg, G. I., Marmer, B. L., Grant, G. A., Eisen, A. Z., Wilhelm, S. M. and He, C. (1989) Proc Natl Acad Sci USA 86:8207–8211.
21. Goldberg, G. I., Strongin, A, Collier, I. E., Genrich, L. T., Marmer, B. L. (1992) J Biol Chem. 267(7):4583–91;
22. Fridman, R., Fuerst, T. R., Bird, R. E., Hoyhtya, M., Oclkuct, M., Kraus, S., Komarek, D., Liotta, L. A., Berman, M. L., Stetler-Stevenson, W. G. (1992) J. Biol. Chem. 267:15398–15405.
23. Willenbrock, F., Murphy G. (1994) American Journal of Respiratory & Critical Care Medicine. 150(6 Pt 2):S165–70.
24. DeClerck, Y. A., Yean, T. D., Lee, Y., Tomich, J. M., Langley, K. E. (1993) Biochemical J 289(Pt 1):65–69.
25. Duangqing Pei and Stephen Weiss, (1996)J. Biol. Chem. 271, 9135–9140.
26. Hiroshi Sato, Takcshi Kinoshita, Takahiso Takino, Kazuo Nakayama, and Motoharu Seiki. (1996) FEBS Letters (in press)
27. Libson, A. M., Gittis, A. G., Collier, I. E., Marmer, B. L., Goldberg, G. I., Lattman, E. E. (1995) Nature, Structural Biology. 2(11):938–942.
28. Jones, T. A., et al., (1991) Acta Crystallogr. 47:110.
29. Li, J., et al., (1995) Structure 15:541–549.
30. Willenbrock, F., ct al., (1993) Biochemistry 32:4330–4337.
31. Williamson, R. A., ct al., (1990) Biochcm. J. 268:267–274.
32. Williamson, R., et al., (1994) Biochemistry 33:11745–11759.
33. Hiroshi Sato, Motoharu Seiki. (1996) A Review J. Biochem. 119, 209–215
34. Brooks, P. C., Stromblad, S., Sanders, L C., von Schalscha, T. L., Aimes, R. T., Stetier-Stevenson, W. G., Quigley, J. P., Cheresh, D. A. (1996) Cell 85:683–693.
35. QUANTA release 4.1.1, (York, England: Molecular Simulations Inc., 1990).
36. Evans, S. V., (1993) SETOR: J. Molec. Graphics 11:134–145.

What is claimed is:

1. A target area for screening test compounds as inhibitors of matrix metalloproteinases consisting of a peptide of residues $Trp^{574}$ to $Asp^{656}$ in the tissue inhibitor of 72 kDa type IV collagenase binding site of the C-terminal domain of gelatinase-A as shown in SEQ ID NO:19.

2. A method of screening a test compound for inhibition of matrix metalloproteineases comprising:
    a) contacting said test compound and said metalloproteinease, and
    b) determining the inhibitory effect of said test compound in a competitive inhibition assay in which displacement of $^{125}I$-labeled peptide bound to the tissue inhibitor of 72 kDa type IV collagenase by unlabeled test compound and unlabeled peptide is measured and the $K_i/K_d$ ratio is determined;
    wherein $K_i/K_d \geq 1$ indicates inhibition, $K_i$ is the inhibitory constant of said test compound, $K_d$ is the dissociation constant of said peptide, and wherein said peptide consists of residues $Trp^{574}$ to $Asp^{656}$ in the tissue inhibitor of 72 kDa type IV collagenase binding site of the C-terminal domain of gelatinase A as shown in SEQ ID NO. 19.

\* \* \* \* \*